US00RE40300E

(19) United States
(12) Reissued Patent
Waldrep et al.

(10) Patent Number: US RE40,300 E
(45) Date of Reissued Patent: May 6, 2008

(54) CARBON DIOXIDE ENHANCEMENT OF INHALATION THERAPY

(75) Inventors: J. Clifford Waldrep, The Woodlands, TX (US); J. Vernon Knight, Houston, TX (US); Nadezhda Koshkina, Houston, TX (US)

(73) Assignee: Research Development Foundation, Carson City, NV (US)

(21) Appl. No.: 10/927,663

(22) Filed: Aug. 26, 2004

Related U.S. Patent Documents

Reissue of:
(64) Patent No.: 6,440,393
Issued: Aug. 27, 2002
Appl. No.: 09/729,468
Filed: Dec. 4, 2000

U.S. Applications:
(60) Provisional application No. 60/169,038, filed on Dec. 4, 1999, now abandoned.

(51) Int. Cl.
*A61K 9/12* (2006.01)
*A61K 9/127* (2006.01)

(52) U.S. Cl. ..... 424/45; 424/450; 424/458; 424/1.13; 424/1.21

(58) Field of Classification Search ..... 424/45, 424/450, 458, 1.13, 1.121
See application file for complete search history.

(56) References Cited

U.S. PATENT DOCUMENTS

| | | | | |
|---|---|---|---|---|
| 5,049,388 | A | 9/1991 | Knight et al. | 424/450 |
| 5,639,441 | A | 6/1997 | Sievers et al. | 424/9.3 |
| 5,958,378 | A | 9/1999 | Waldrep et al. | 424/45 |
| 6,090,407 | A | 7/2000 | Knight et al. | 424/450 |
| 6,106,859 | A | 8/2000 | Desmore, Jr. et al. | 424/450 |

OTHER PUBLICATIONS

Davis and Staag, "Interrelationships of volume and time components of individual breaths in resting man," *J. Physiol.*,245:481, 1975.

Densmore et al., "Gene transfer by guanidinium–cholesterol: dioleoylphosphatidyl–ethanolamine liposome–DNA complexex in aerosol," *J. Gene Med.*,1:251–264, 1999.

Knight et al., "Anticancer effect of 9–nitrocamptothecin liposome aerosol on human cancer xenografts in nude mice," *Cancer Chemother. Pharmacol.,* 44:177–186, 1999.

Koshkina et al., "Distribution of camptothecin after delivery as a liposome aerosol or following intramuscular injection in mice," *Cancer Chemother. Pharmacol.,* 44:187–192, 1999.

Nielsen et al., "Ventilation, $CO_2$ Production, and $CO_2$ Exposure Effects in Conscious, Restrained CF–1 Mice," *Pharmacol. & Toxicol.,* 72:163–168, 1993.

Persons et al., "Airway deposition of hygroscopic heterodispersed aerosols: results of a computer model," *J. Appl. Physiol.,* 63:1195–1204, 1987.

Persons et al., "Maximization of pulmonary hygroscopic aerosol deposition," *J. Appl. Physiol.* 63:1205–1209, 1987.

Schlenker, "Ventilation and Metabolism of the Djungarian Hamster (*Phodopus Sungorus*) and the Albino Mouse," *Comp. Biochem. Physiol.,* 82A(2):293–295, 1985.

Stegen et al., "Negative affect, respiratory reactivity, and somatic complaints in a $CO_2$ enriched air inhalation paradigm," *Biol. Psychol.* 49:109–122, 1998.

Vidgren et al., "A study of $^{99m}$technetium–labelled beclomethasone dipropionate dilauroylphosphatidylcholine liposome aerosol in normal volunteers," *Int. J. Pharm.,* 115:209, 1995.

Waldrep et al., "High dose cyclosporin A and budesonide–liposome aerosols," *Int. J. Pharm.,* 12:27, 1997.

Co–Pending U.S. Appl. No. 09/540,916, filed Mar. 31, 2000.

Kim et al, International Journal of Pharmaceutics, 180(Dec. 1998) pp. 75–81, Pharmacodynamics of insulin in polyrthylene glycol–coated liposomes.*

* cited by examiner

*Primary Examiner*—Johann Richter
*Assistant Examiner*—Mina Haghighatian
(74) *Attorney, Agent, or Firm*—Fulbright & Jaworski, L.L.P.

(57) ABSTRACT

The present invention provides a method of increasing the deposition of aerosolized drug in the respiratory tract of an individual or animal, comprising the step of administering said aerosolized drug in an air mixture containing up to about 10% carbon dioxide gas.

52 Claims, 15 Drawing Sheets

CARBON DIOXIDE ENHANCEMENT OF INHALATION THERAPY

Matter enclosed in heavy brackets [ ] appears in the original patent but forms no part of this reissue specification; matter printed in italics indicates the additions made by reissue.

CROSS-REFERENCE TO RELATED APPLICATION

This patent application claims benefit of priority of provisional application, U.S. Ser. No. 60/169,038, filed Dec. 4, 1999, now abandoned.

BACKGROUND OF THE INVENTION

1. Field of the Invention

The present invention relates generally to the fields of pharmacology and drug delivery. More specifically, the present invention relates to a method of using carbon dioxide gas to increase pulmonary deposition of an aerosolized drug during inhalation therapy.

2. Description of the Related Art

Small particle liposome aerosol treatment consists of lipid-soluble or water-soluble anti-cancer drugs incorporated into liposomes, which are administered from aqueous dispersions in a jet nebulizer (see U.S. Pat. No. 5,049,388). Aerosols of 1-3 μm mass median aerodynamic diameter, generated upon nebulization, enable targeted delivery onto surfaces of the respiratory tract. The deposited liposomes subsequently release drug locally within the lung or into the blood circulation with delivery to extra-pulmonary tissue.

If the drug is lipid soluble, it will associate with the lipid molecules in a manner specific to the lipid employed, the anti-cancer drug employed and possibly it may be modified further by various soluble constituents which may be included in the suspending aqueous medium. Such soluble constituents may include buffering salts and possibly inositol to enhance the synthesis and secretion of surfactant phospholipid in lung tissue and to minimize respiratory distress already present or that which might result from the aerosol treatment (7).

If the drug is water soluble, it may be incorporated by appropriate procedures in aqueous vesicles that exit in concentric spaces between lipid bilayers (lamellae) of the multilamellar liposome. Unilamellar liposomes may be prepared; however, their capacity to entrap either lipid-soluble or water-soluble drugs is diminished since entrapment is restricted to one central vesicle. Aerosol water droplets may contain one or more drug-liposomes. Moreover, it is also possible to incorporate more than one drug in a aerosol liposome treatment, either by mixing different drug-containing liposomes, or by using liposomes wherein the drugs have been combined and incorporated together into liposomes.

Nebulization shears liposomes to sizes readily discharged from the nozzle of the nebulizer. Liposomes up to several microns in diameter are typically sheared to diameters of less than 500 nm, and may be considerably smaller than that depending on the operating characteristics of the nebulizer and other variables. Shearing of water-soluble drugs contained in liposomes will release appreciable amounts of the water soluble compound, perhaps 50 percent. This is not a contraindication to their use, but it means that two forms of the drug preparation is administered, and the effect includes the therapeutic effect that would be produced by both forms if either form has been given alone. Many other details of liposome aerosol treatment are described in U.S. Pat. No. 5,049,388.

In general, the underlying objective of inhalation therapy is the topical delivery of aerosolized particles of pharmaceutical drugs into the central airways and to peripheral regions of the respiratory tract. However, the deposition fraction of the inhaled particles even for the optimal size range of 1-2 μm mass median aerodynamic diameter is only approximately 20%. Pulmonary deposition of inhaled aerosols is influenced significantly by particle size, hygroscopic properties and airway geometry (1,2). The breathing pattern is also an important variable that determines the deposition pattern of inhaled particles (1,2).

Specifically, breath holding markedly increases pulmonary deposition due to increased residence time of particles within the lung. This allows a longer period for gravity sedimentation to occur especially in the small peripheral airways and to ensure that the aqueous particles can equilibrate fully in the near 100% humidity and reach their maximum size, which further enhances their deposition (1,2). Computer simulations demonstrate that a thirty-second breath holding maneuver in humans can increase the deposition fraction 3.2 times. The physiological principle of this effect is due to increased particle intake upon deep inspiration in which the inhaled volume may be as much as 8-fold higher than the amount inhaled with basal tidal breathing. This larger volume of tidal breathing leads to penetration of particles to the furthest recesses of the lung where airway diameters are smallest, and thus deposition due to gravity and maximum particle size occurs with greatest efficiency.

By extension of this physiological property, direct utilization of factors which could increase the volume of inspired air (containing aerosol particles) would subsequently markedly increase the deposited fraction in the central airway and to an even greater extent in the peripheral lung. Carbon dioxide ($CO_2$) is the most important natural regulator of respiration. Carbon dioxide diffuses freely from the tissues into the blood according to the existing pressure gradient. Increased levels of carbon dioxide in the blood readily diffuse into the cerebrospinal fluid where there is conversion into $HCO_3^-$ and $H^+$. Central chemoreceptors on the ventral surface of the medulla respond to increased $H^+$ in the CSF and cause a compensatory increase in ventilation (rate and tidal volume).

Investigators have utilized carbon dioxide inhalation to manipulate ventilation in experimental animals and humans. Inhalation of 5% carbon dioxide causes as much as 192% increase in tidal volume (3). This increase is rapid and reaches a sustained plateau throughout the duration of exposure (4). Once the carbon dioxide exposure ceases, the changes in ventilation reverse within minutes to basal level (4). Similarly, inhalation of 5% carbon dioxide by humans results in a 3-fold increase in the minute volume (5). Inhalation of 5% or 7.5% of carbon dioxide by normal humans for two minutes resulted in increases in frequency of breathing by 6.7% and 19%, respectively, and increases in tidal volumes by 31% and 52%, respectively, so that minute volumes were increased by 34% and 75%, respectively (6). Longer exposures to these concentrations would have produced even greater responses (5).

Camptothecin analogues and taxanes are chemical agents currently being developed as chemotherapeutic agents (21, 26). The anticancer drugs, paclitaxel (PTX) and different camptothecin (CPT) derivatives are clinically active in the treatment of a variety of human tumors, including lung cancer. These drugs show beneficial results in clinical trails when used as single agents or in combination with other drugs (21). These drugs are given systemically by oral or intravenous routes of administration; the most effective route for paclitaxel is continuous intravenous infusion (22, 24) whereas lipophilic congeners of camptothecin administrated orally prove most effective. The development of toxic side effects is often a major limitation in such therapeutic regimens. Several subcutaneous human cancer xenografts in nude mice (23) and in experimental murine pulmonary metastasis (6) have been successfully treated using liposomal formulations of camptothecin and 9-nitrocamptothecin (9NC) administered by the aerosol route as an alternative method of therapy. Pharmacokinetic studies in mice with camptothecin showed that inhalation of liposomal camptothecin produced substantial drug levels in the lungs and other organs, which cleared rapidly after cessation of aerosol delivery (17). In spite of these levels, aerosol delivery systems are generally only 15-20% efficient in drug deposition (29, 30); thus increasing pulmonary deposition would be advantageous.

Using these systemic routes of drug delivery, a certain amount of drug egresses from the blood stream and localizes in the respiratory tissue, but lungs are not the main organs for drug deposition. The utilization of conventional liposomes are carriers for these drugs does not improve the pulmonary deposition of drugs administered by commonly used systemic routes ( 11,27). Nebulization is a very effective route for target drug delivery to the respiratory tract (17); e.g., camptothecin. Dogs with spontaneously arising primary and metastatic lung tumors have been successfully treated when new formulations of doxorubicin and PTX are delivered via aerosolization (16). However in these instances, aerosols were generated using normal air.

Gene delivery to different tissues has been accomplished using both viral and nonviral vectors. Although the use of nonviral vectors avoids the immunogenic response associated with viral vectors, nonviral vectors, such as cationic lipids and polycationic polymers, have not been associated generally with the high levels of gene expression characteristic of viral vectors. However, polyethyleneimine (PEI), a cationic polymer, is effective both in tissue culture and in vivo (36). The protonable nitrogen on every third nitrogen provides polyethyleneimine with a huge buffering capacity. Polyethyleneimine can effectively traffic DNA to the nucleus (37) and protect DNA against DNAse degradation (36). Both linear and branched forms of polyethyleneimine have been shown to produce high levels of transgene expression in various tissues such as lung, brain, and kidney (39-41). Polyethyleneimine has also been used to efficiently deliver DNA to tumors in vivo (42).

Aerosol delivery is a noninvasive way to deliver genes of interest to the lungs and could potentially be used to treat diseases such as lung cancer and cystic fibrosis. However, the levels of transgene expression have not been very high due, in some cases, to loss of DNA viability during nebulization (43). PEI can protect the DNA during nebulization (44) and can result in higher levels of transfection in the lung than most of the other cationic lipids tested (44,45). PEI-mediated transfection is also resistant to inhibition by lung surfactants (46).

Increased efficiency of drug deposition to the respiratory tract by the inhalation route is achieved by several ways: 1) changing the concentration of drug in the formulation used for aerosolization (31); 2) using more efficient types of nebulizers (32); 3) increasing the duration of treatment; or 4) changing the breathing patterns (4). As previously stated, carbon dioxide is a natural modulator of respiration. The inhalation of air containing low concentrations of $CO_2$ (from about 3-7%) caused similar changes in breathing patterns and was tolerated well (13, 6). No difference in breathing patterns was observed between inhalation of 5% $CO_2$-in-air and moderate physical exercise in man (32). Similar effects of 5% $CO_2$-in-air may be obtained in man using aerosol treatment. Thus utilization of $CO_2$-enriched air for nebulization as a modulator of inhalation therapy can result in more effective pulmonary delivery of chemotherapeutic agents.

The prior art is deficient in the lack of a means of enhancing the pulmonary deposition of an aerosolized drug during inhalation therapy. The present invention fulfills this longstanding need and desire in the art.

SUMMARY OF THE INVENTION

The present invention provides a method of increasing the deposition of aerosolized drug in the respiratory tract of an individual or animal, comprising the step of administering said aerosolized drug in an air mixture containing up to about 10% carbon dioxide gas. 2.5%, 5%, and 7.5% carbon dioxide concentrations have been used herein. The aerosol may be administered for 1 to 30 minutes or even longer. The administered drug may be a soluble drug, an insoluble drug or a therapeutic composition, e.g., oligonucleotide, gene, peptide, or protein, that may be dissolved in solution and directly aerosolized with a jet nebulizer or incorporated into a carrier such as liposomes, slow release polymers or polycationic polymers prior to aerosolization.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

For each time point lungs from three mice are combined and the drug content determined by HPLC. Each experiment is repeated three times and mean values with SD are calculated.

Figure 4:
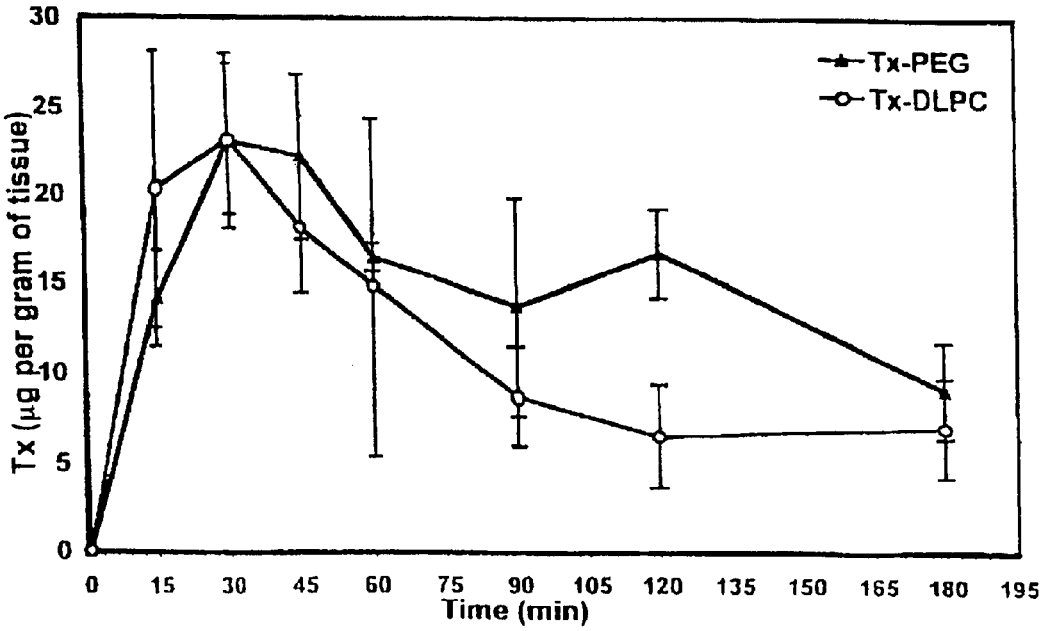

FIG. 4 shows the comparison of tissue paclitaxel levels in the lungs of mice exposed to aerosols containing different liposomal formulations. Equivalent levels of exposure to paclitaxel are achieved in a 5% $CO_2$-in-air aerosol of sterically stabilized paclitaxel-liposomes prepared from dimyristylphosphoethanolamine poly (ethylene glycol) 2000 as when DLPC is utilized.

Figure 5:
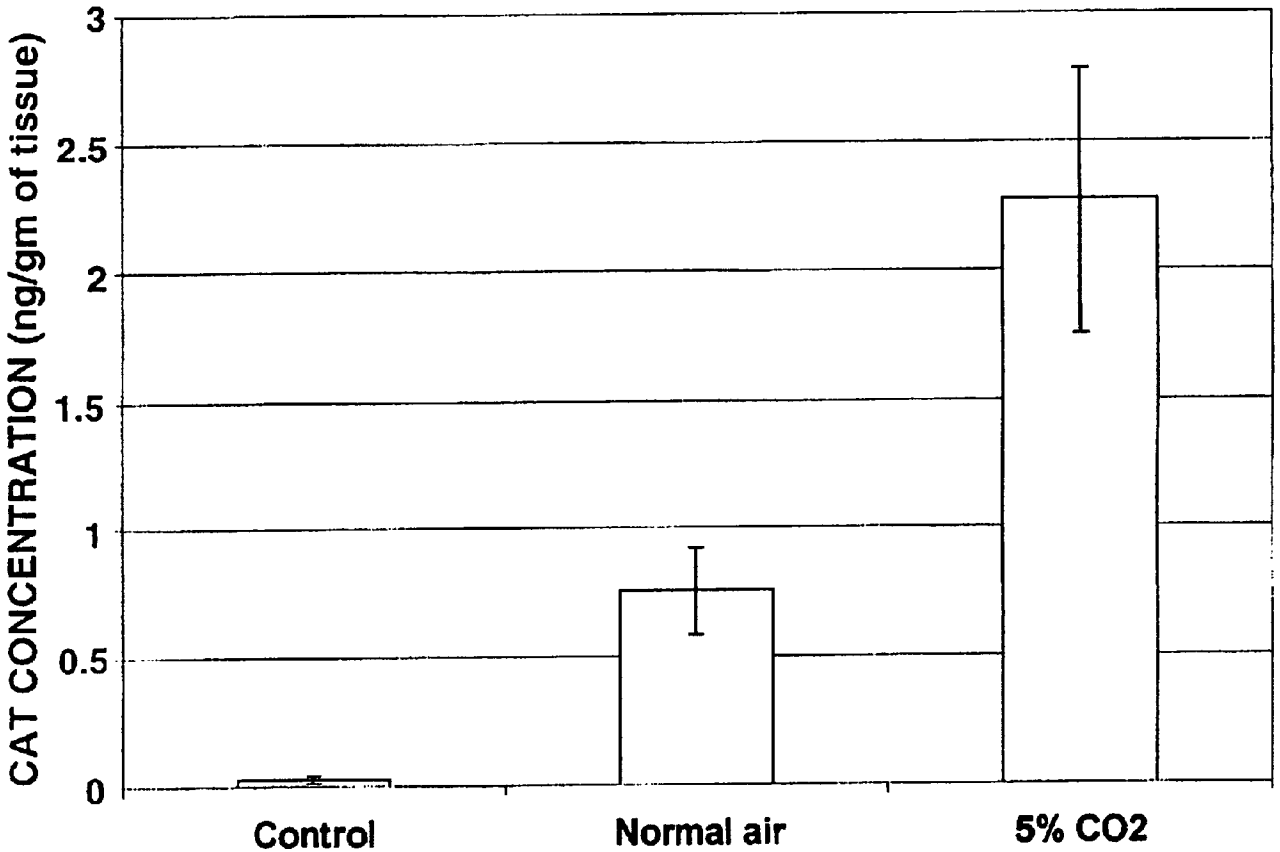

FIG. 5 shows the comparison between CAT expression in lung by PEI-DNA aerosol generated using air or air containing 5% $CO_2$. One milligram of CAT plasmid was complexed with PEI at an N:P ratio of 10:1 and the resulting complex aerosolized to mice for 30 min. The lungs are harvested after 24 h and the CAT assay is performed as described. Values are means±SD (n=6 mice per group, P=0.001).

Figure 6:
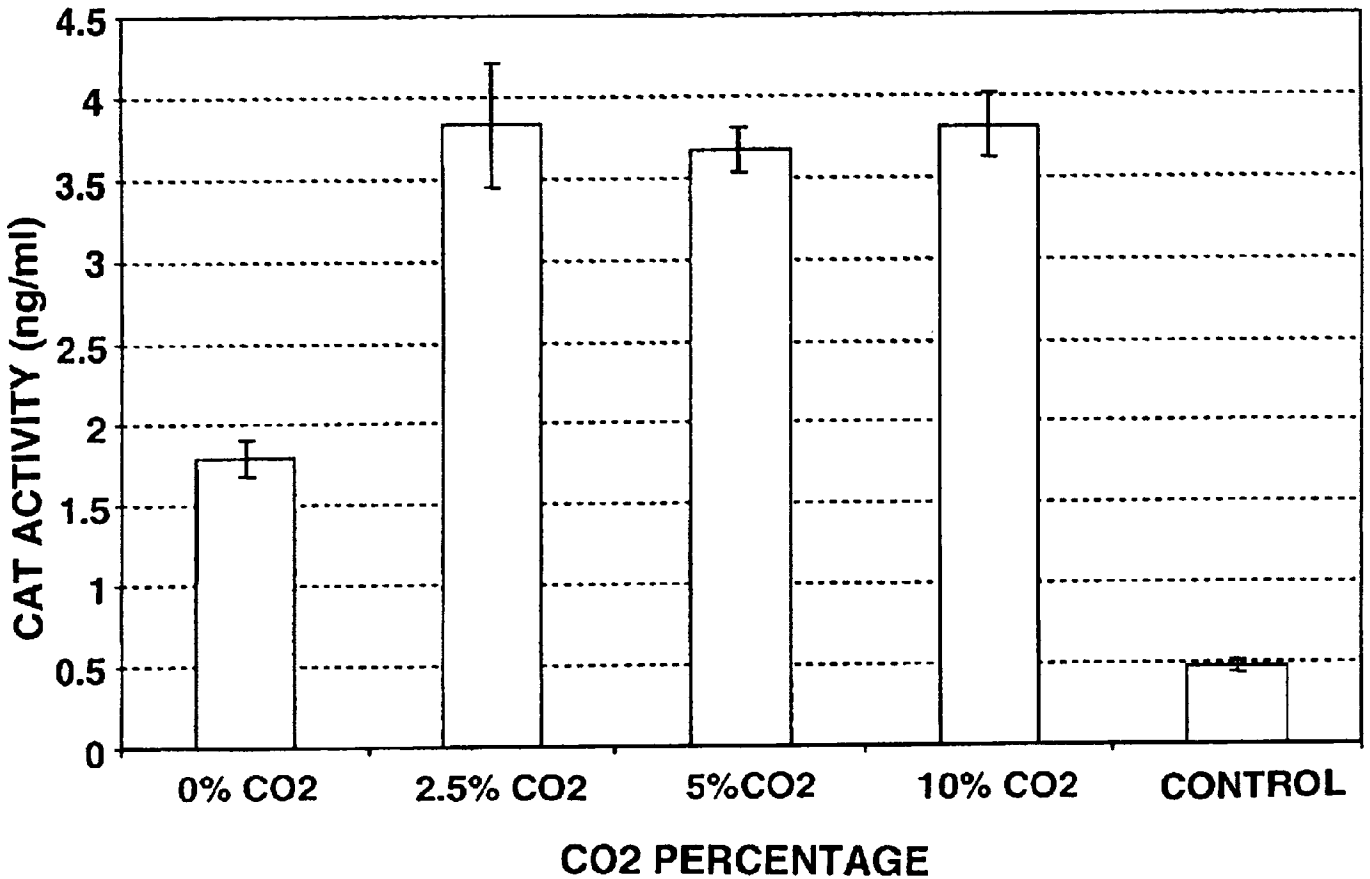

FIG. 6 shows the effect of percent CO2 on the efficiency of PEI-DNA transfer to the lung by aerosol. Different percentages of CO2-in-air are used with a fixed amount of CAT plasmid. The complexes were aerosolized using 0%, 2.5%, 5%, 10% carbon dioxide and control. Mice are sacrificed, the lungs harvested, and the CAT assay was performed. Values are expressed as means±SD.

Figure 7:
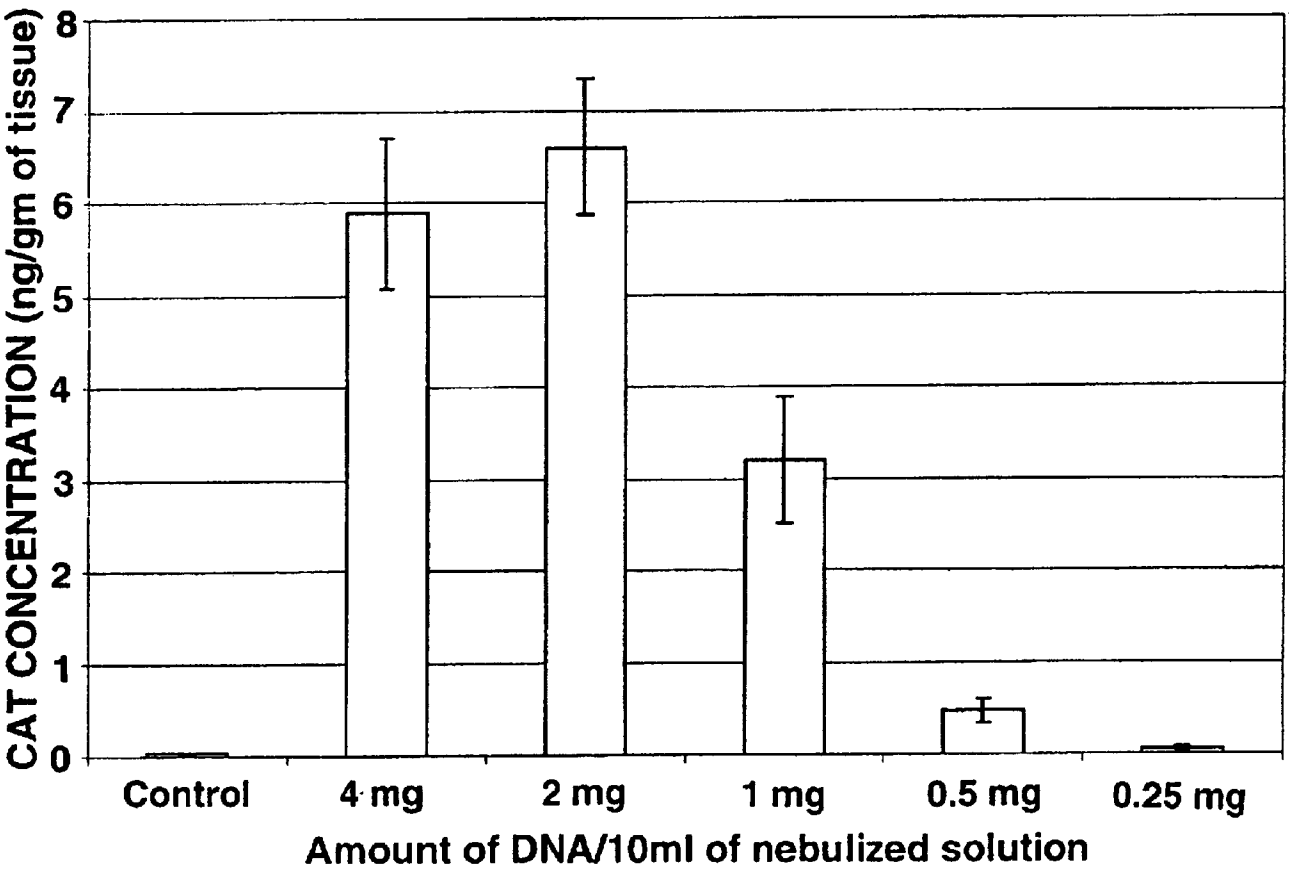

FIG. 7 shows that the gene expression in lung by PEI-DNA aerosol was dose dependent. Increasing doses of CAT plasmid were aerosolized using 5% $CO_2$-in-air at a fixed N:P ratio of 10:1. There is an increase in both the total amount of DNA delivered and the concentration of PEI-DNA delivered. Mice were sacrificed after 24 h, the lungs are harvested, and the Cat protein is assayed. Values are means±SD (n=5 mice per group).

Figure 8:
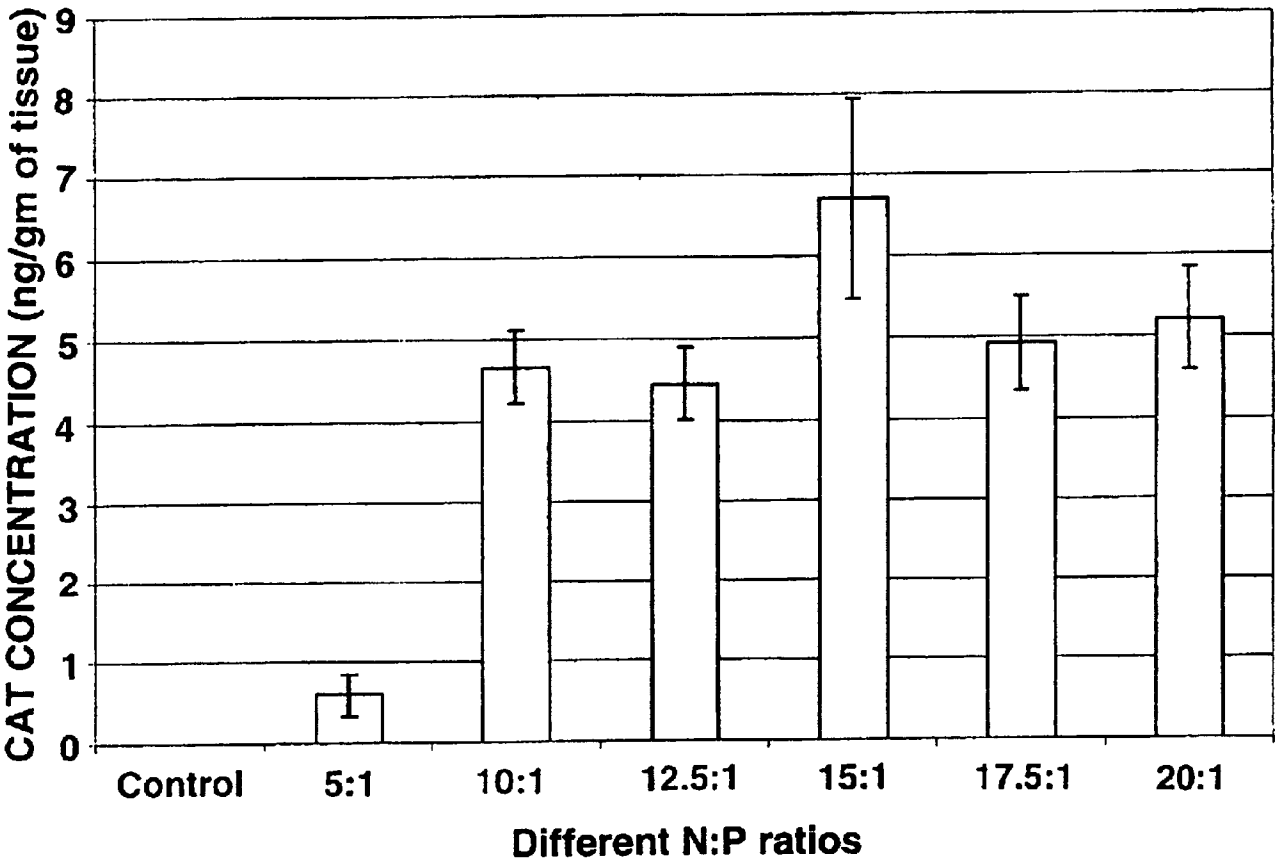

FIG. 8 shows the effect of N:P ratios on the efficiency of PEI-DNA transfer to the lung by aerosol. Different PEI-DNA(N:P) ratios are used with a fixed amount CAT plasmid (2 mg). The complex is aerosolized using 5% $CO_2$-in-air. Mice are sacrificed after 24 h, the lungs are harvested, and the CAT assay is performed. Values are means±SD (n=5 mice per group).

Figure 9:
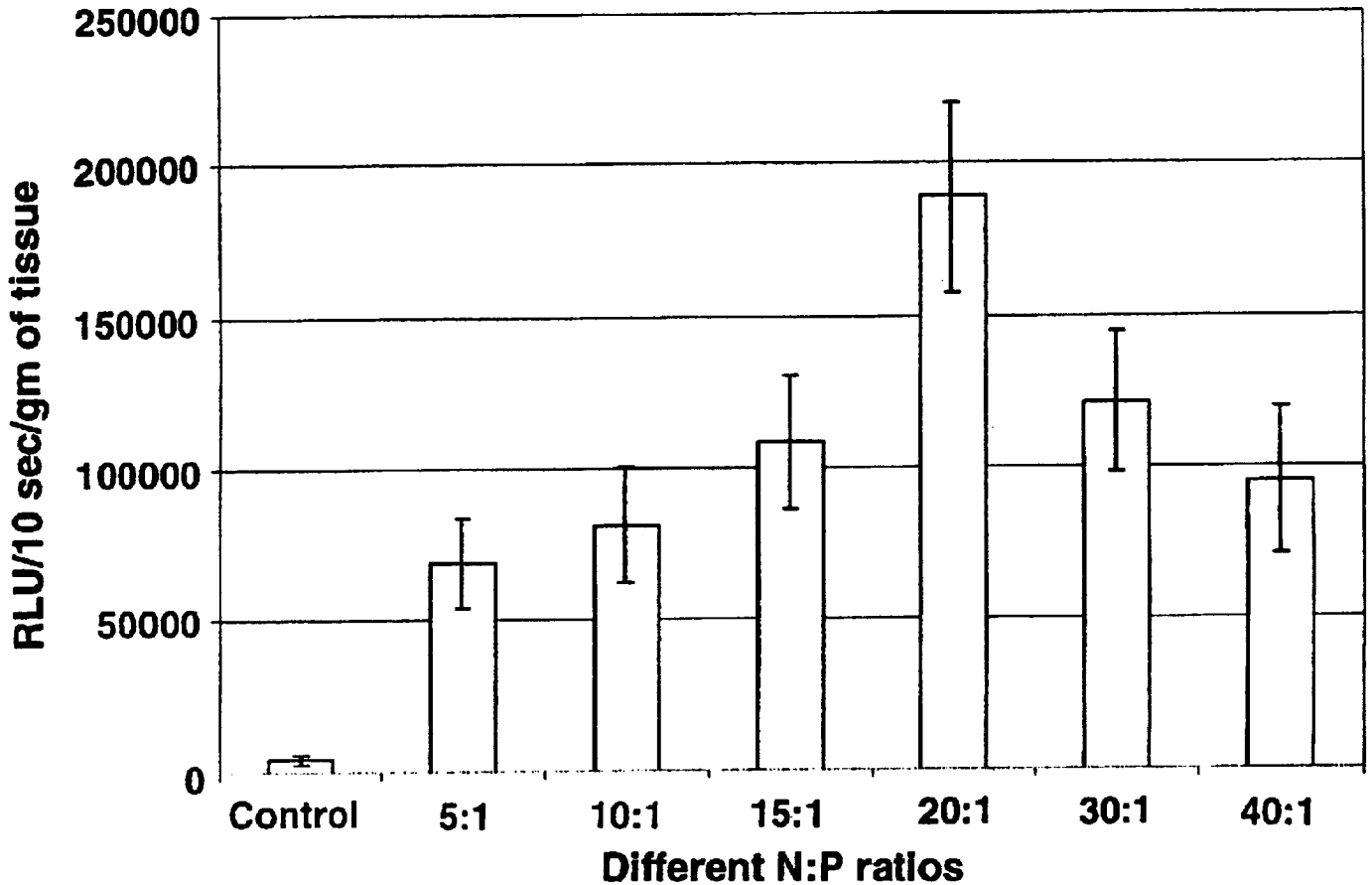

FIG. 9 shows the effect of N:P ratios on luciferase gene expression in the lung. A fixed amount of luciferase plasmid (2 mg) is delivered at different N:P ratios. The complexes are aerosolized using 5% $CO_2$-in-air. Mice are sacrificed 24 h after aerosol delivery, lungs are harvested, and luciferase activity is determined. Values are means±SD (n=5 mice per group).

FIG. 10 shows the time course of transgene expression after single PEI-DNA aerosol exposure.

Figure 10A:
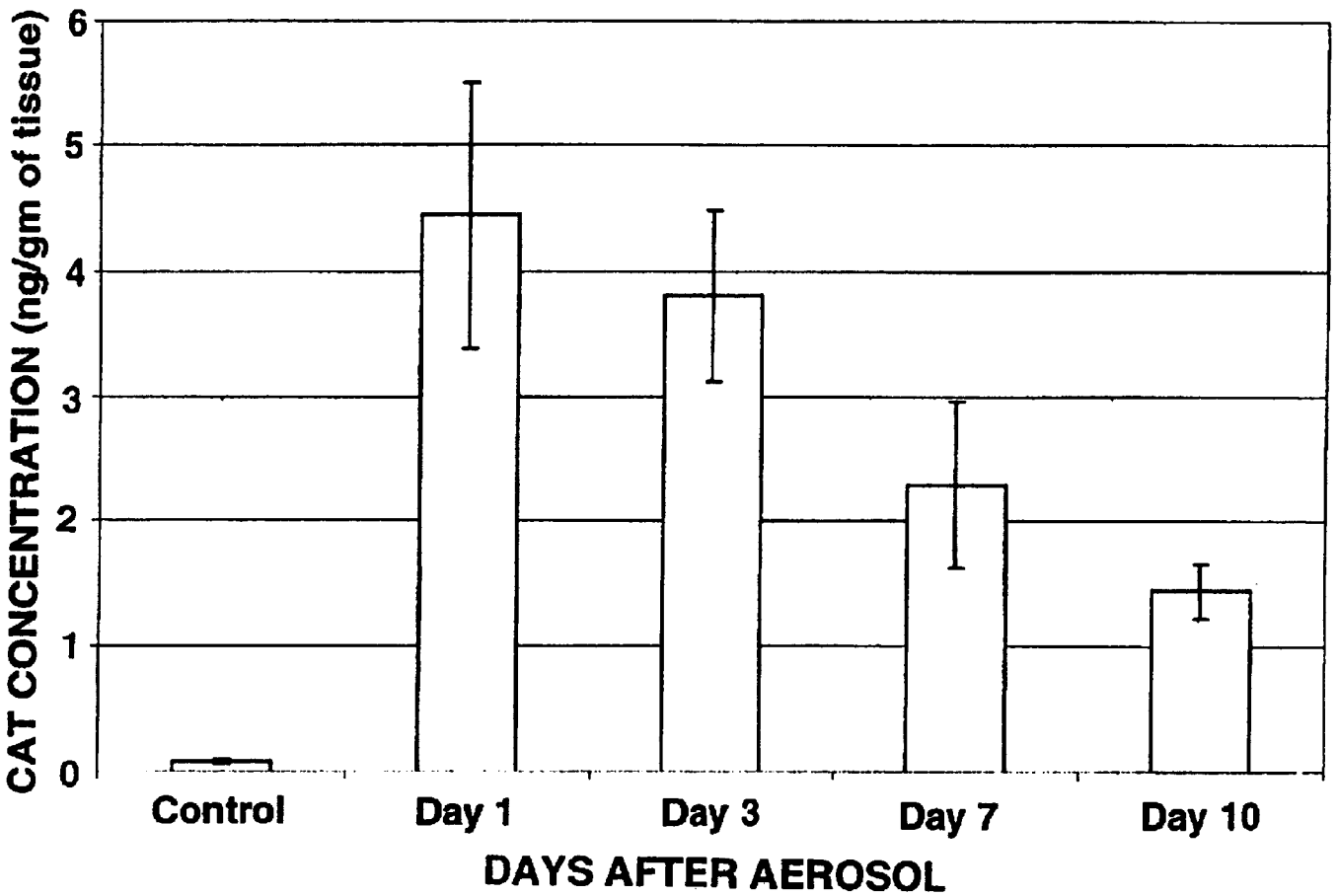

In FIG. 10A mice are delivered an aerosol containing 2 mg of CAT plasmid at a N:P ratio of 15:1 using 5% $CO_2$-in-air. Mice are sacrificed at different time points and the lungs are harvested and immediately frozen. The CAT assay is performed after the last time point. Values are means±SD (n=5 mice per time point).

Figure 10B:
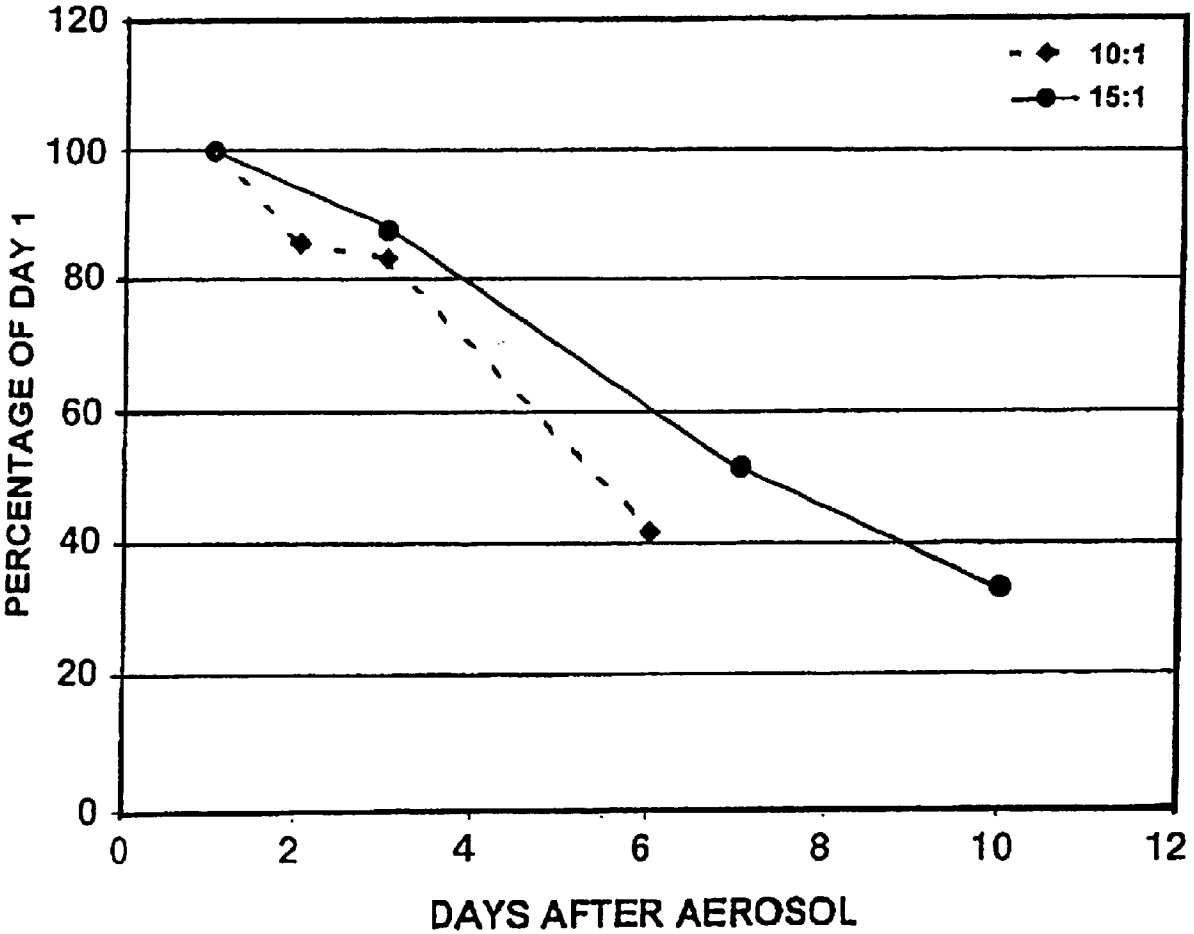

FIG. 10B shows the persistence of CAT expression using two different N:P ratios. Both groups of mice (n=5 mice each per time point per group) are delivered 2 mg of CAT plasmid at a 15:1 or 10:1 NPP ratio using 5% $CO_2$-in-air. The time points for the 10:1 ratio are 1, 2, 3, and 6 days post aerosol exposure and for the 15:1 ratio are 1, 3, 7, and 10 days post aerosol exposure.

Figure 11:
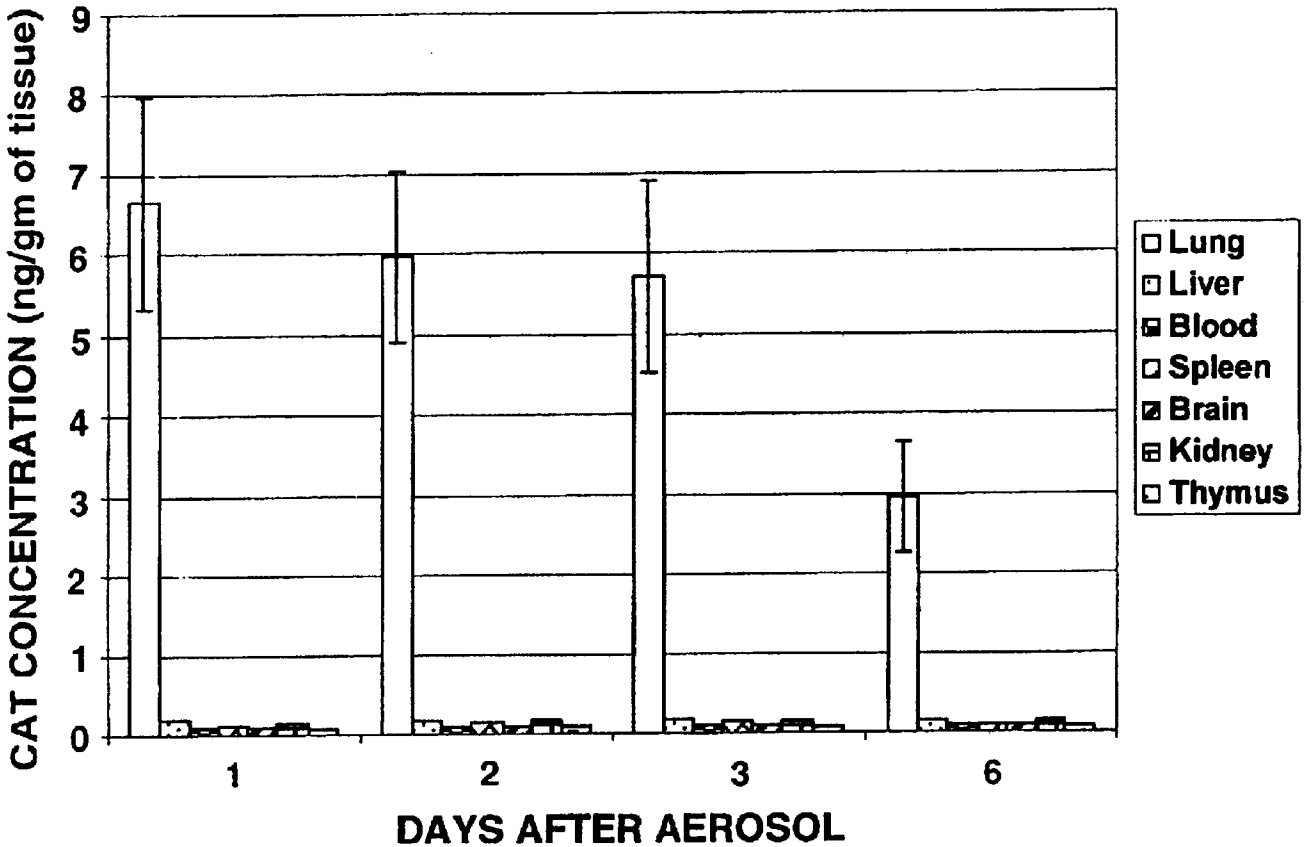

FIG. 11 shows tissue distribution of transgene after single PEI-DNA aerosol exposure. The same groups of mice are used as in FIG. 9 (from the 10:1 group). Different tissues are harvested and immediately frozen. The CAT protein is assayed after the last time point. Values are means±SD (n=5 mice per time point). Levels of CAT in non-lung tissues in the aerosol-exposed group are not different from the control tissues (P>0.1).

Figure 12A:
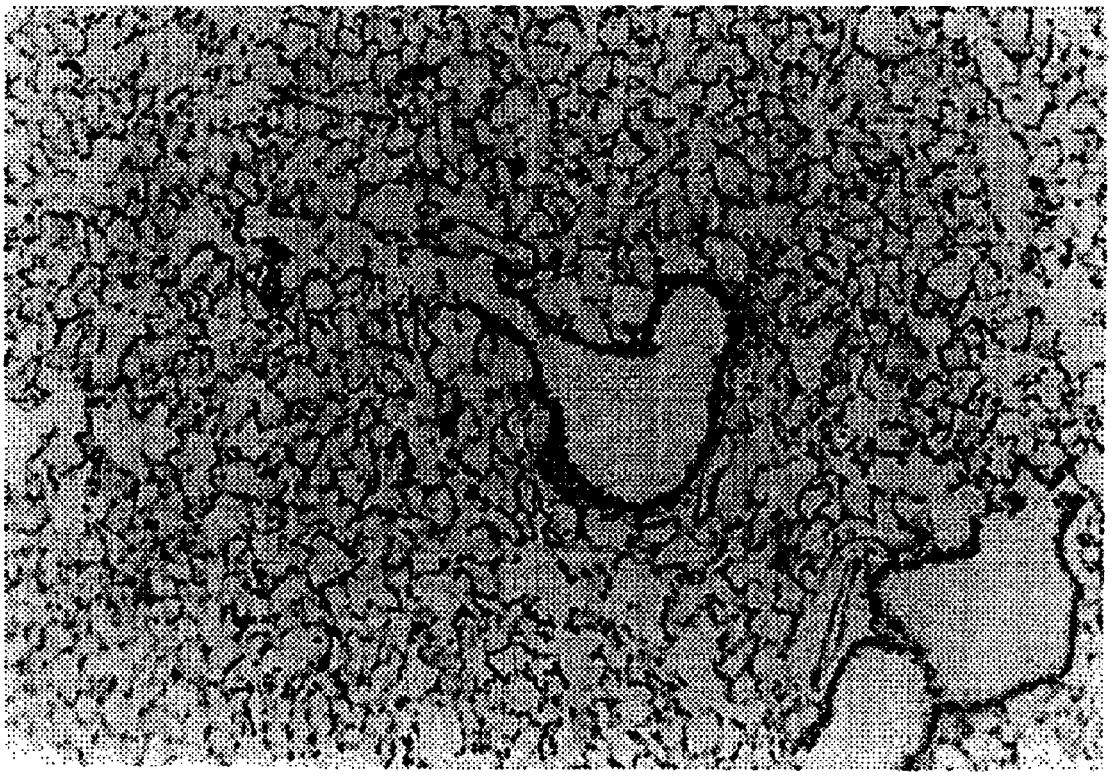
Figure 12B:
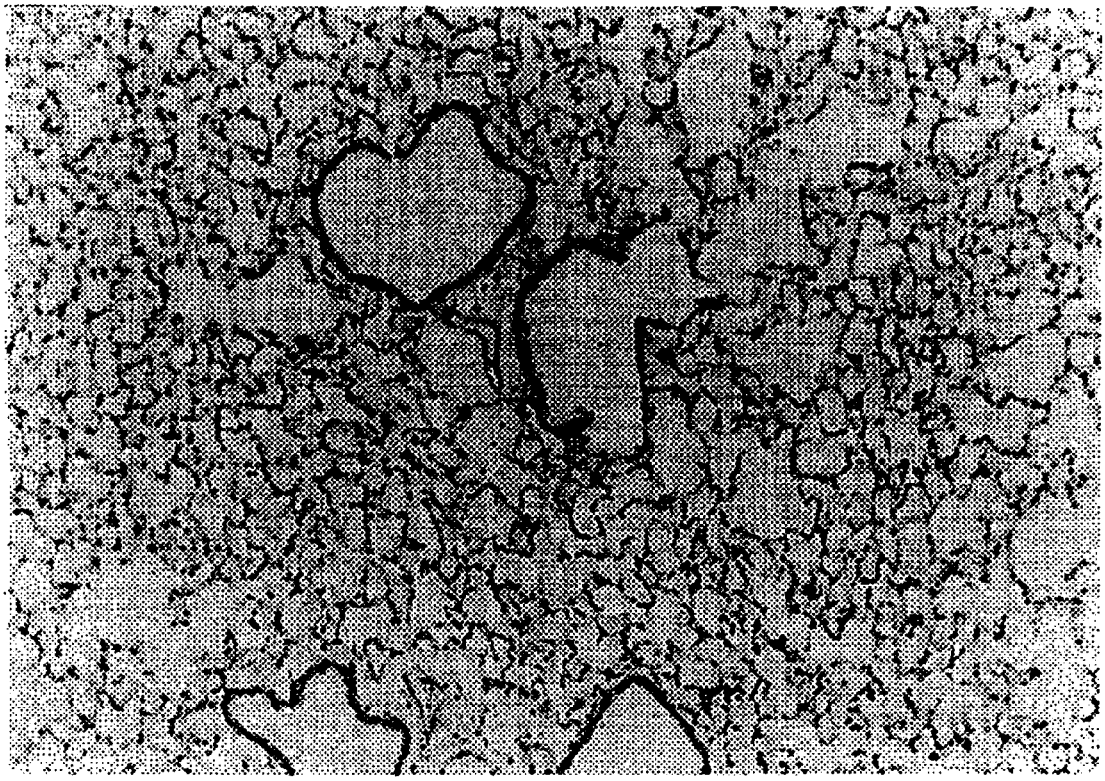

FIG. 12 shows the histologcial analysis of PEI-DNA aerosol-treated lungs. Two milligrams of CAT plasmid is complexed with PEI at a N:P ratio of 15:1 and the complex was aerosolized to five mice for 30 min using 5% $CO_2$-in-air. Mice are sacrificed 24 h later and lungs are harvested and fixed in formalin. Thin sections are stained with hemtoxylin and eosin (H&E). FIG. 12A: bronchiole (control); FIG. 12B: bronchiole (treated). Magnification 100×.

FIG. 13 shows the inhibition of B16-F10 lung metastasis by PEI-p53 aerosol delivery.

Figure 13A:
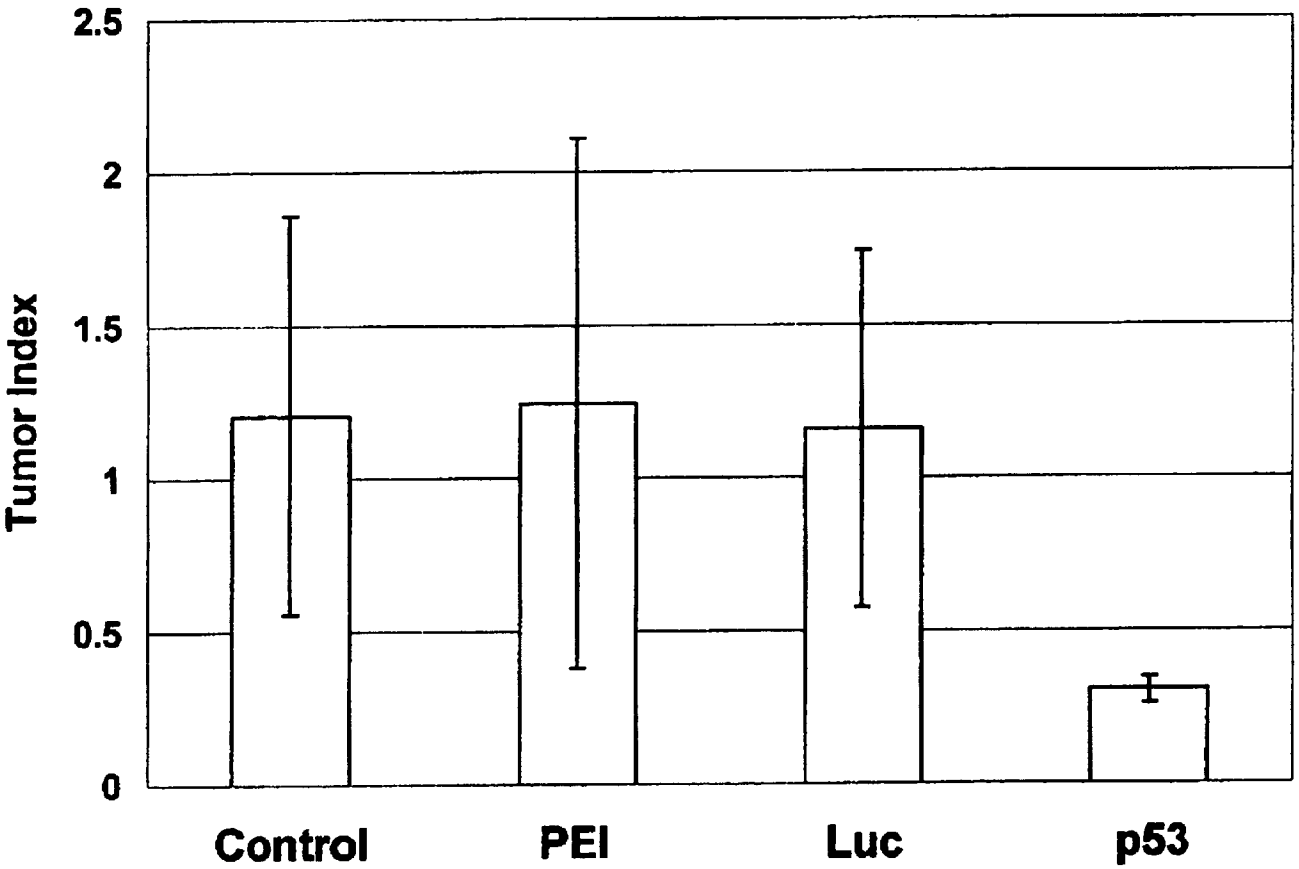

FIG. 13A: Tumor index was calculated by the formula: Tumor index=lung weights×average grade for the group. Values are means±SD (n=10 mice per group).

Figure 13B:
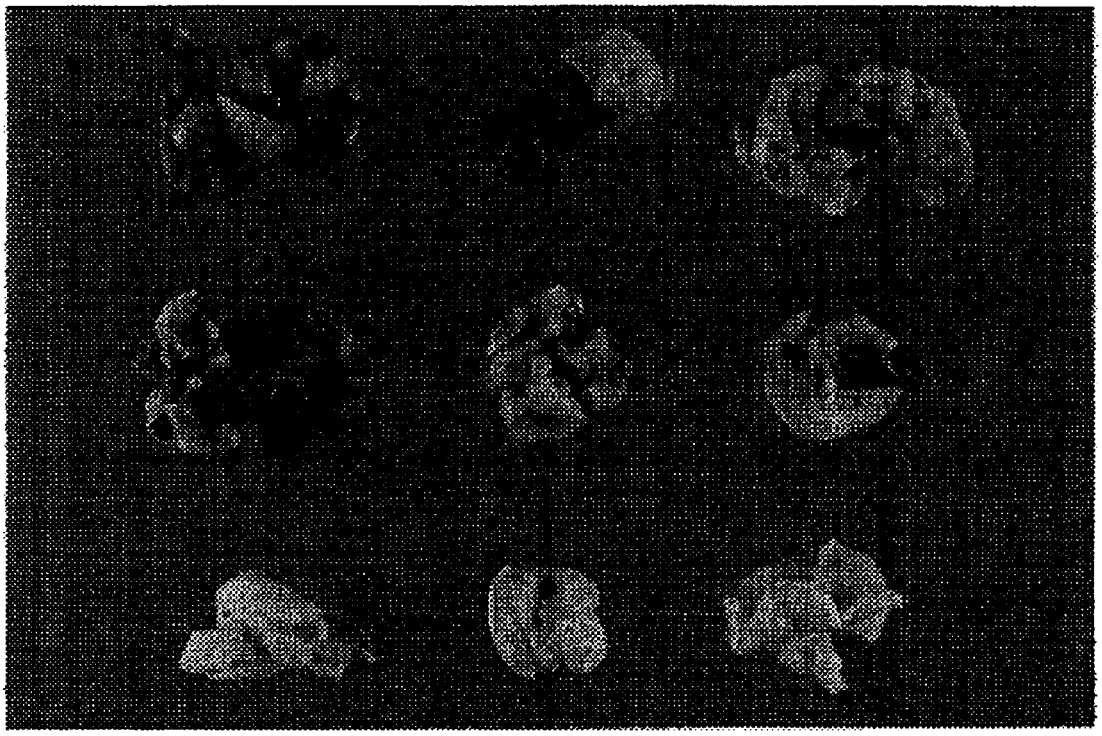

FIG. 13B: Representative lungs from control, PEI-Lucand PEI-p53 treated mice are presented (n=10 mice per group). Lungs from PEI-treated group (not shown) are similar in shape, size, and number of tumor foci to those shown for control and PEI-Luc-treated groups. Data are representative of two separate experiments.

Figure 13C:
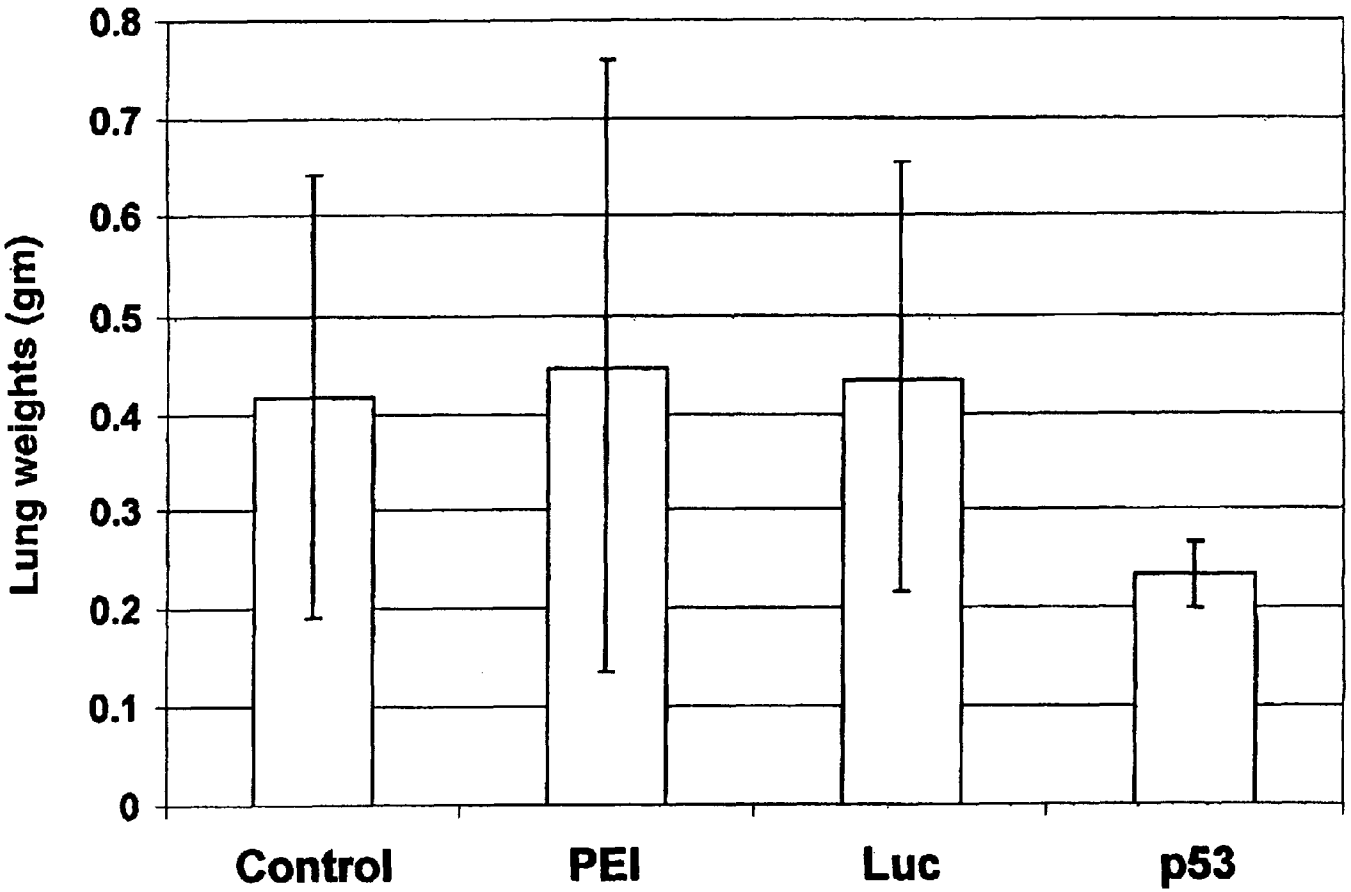

FIG. 13C: Lung weights of mice from different groups. Values are means±SD (n=10 mice per group).

DETAILED DESCRIPTION OF THE INVENTION

The present invention provides a method of increasing the deposition of aerosolized drug in the respiratory tract of an individual or animal, comprising the step of administering said aerosolized drug in an air mixture containing up to about 10% carbon dioxide gas. Preferred concentrations include 2.5%, 5% and 7.5% carbon dioxide gas. The aerosol may be administered for 1 to 30 minutes or even longer.

The instant invention is directed to the aerosol delivery of a water soluble drug. Such a drug may be directly prepared as a water solution or a buffered solution and directly aerosolized. Representative water soluble drugs include antibiotics like tobramycin and pentamidine; muclolytics like acetyl cytsteine; bronchodilators like albuterol; parasympathetic agents like ipratropium bromide; enzymes like DNase; and anti-virals like ribavirin.

Alternatively, the instant invention may be used to deliver an insoluble drug that is associated with a carrier prior to aerosol delivery. Possible carriers include liposomes, slow release polymers and polycationic polymers. Liposomes are an especially useful carrier for lipophilic drugs such as amphotericin B; nystatin; glucocorticoids; immunosuppressives like CsA, FK506, rapamycin or mycophenolate; and anti-cancer drugs like camptothecin, camptothecin derivatives, and paclitaxel. The liposomes may be formed from such lipids as the phospholipid dilauroylphosphatidylcholine (DLPC) or they may be sterically stabilized liposomes formulated with modified phospholipids such as dimyristylphosphoethanolamine poly(ethylene glycol) 2000. Slow release polymers, such as poly(lactic acid-co-glycolic acid) (PLGA), or polycationic polymers, such as polyethyleneimine (PEI), may be utilized.

The instant invention may also be applied to the delivery of therapeutic proteins, therapeutic peptides, DNA genes, sense oligonucleotides, anti-sense oligonucleotides, and viral vectors. Representative examples of DNA genes are the chloramphenical acetyl tranferase gene (CAT) or the p53 gene. Preferably, these genes are delivered via a polycationic polymer carrier such as polyethylenimine. Cationic liposomes also may be utilized as carriers. The polyethylenimine may have a nitrogen:phosphate ratio from about 10:1 to about 20:1. In a preferred embodiment, the PEI nitrogen:phosphate ratio is about 10:1.

The following definitions are provided. Terms not specifically defined area meant to be interpreted as is customary in the art.

As used herein, the term "aerosols" refers to dispersions in air of solid or liquid particles, of fine enough particle size and consequent low setting velocities to have relative airborne stability (8).

As used herein, the term "liposome aerosols" refers to aqueous droplets within which are dispersed one or more particles of liposomes or liposomes containing one or more medications intended for delivery to the respiratory tract of humans or animals (9).

As used herein, the size of the aerosol droplets defined for this application are those described in U.S. Pat. No. 5,049,338, namely mass median aerodynamic diameter (MMAD) of 1-3 μm with a geometric standard deviation of about 1.8-2.2. However, with low concentrations of 9-NC and possibly other camptothecin derivatives, the mass median aerodynamic diameter may be less than 1 μm, such as 0.8 μm. Based on the studies disclosed by the present invention, the liposomes may constitute substantially all of the volume of the droplet when it has equilibrated to ambient relative humidity.

As used herein, the "Weibel Lung Model" refers to a classification of the structure of the human lungs that recognizes 23 consecutive branchings of the airways of humans. The trachea is labeled 0, bronchi and bronchioles extend through branches 16. These portions of the airways contain ciliated epithelium and mucus glands. Together they constitute the mucociliary blanket. Branchings 17-23 compose the alveolar portion of the lung and do not have a mucociliary blanket. Thus, particles deposited here are not carried up the airway to be swallowed.

It is postulated herein that under controlled experimental conditions of hypercapnia, deposition of inhaled drug particles would greatly increase over levels observed during basal tidal breathing conditions. The use of carbon dioxide gas/air mixtures to drive continuous flow jet nebulizers could greatly increase the efficiency of the drug dose delivered to the peripheral lung (Weibel's generations 17-23). By analogy, this system could be effectively utilized to increase the biological efficiency of inhaled drugs. This concept could be theoretically employed with any drug, gene, oligonucleotide, or protein/peptide formulation (soluble, liposomal, crystalline, or polymer-based carrier such as polyethylenimine) and any gas or air driven jet nebulizer The current invention is primarily directed toward the use of carbon dioxide gas to increase the depth and frequency of breathing during inhalation therapy with as aerosolized drug to result in increased minute volumes. The increased tidal lung volume results in enhanced pulmonary deposition of the inhaled drug particles, particularly in the lung periphery which may not be fully ventilated at low levels of breathing. The increased minute volume resulting from increased frequency and greater depth of breathing both contribute to the increased minute volume.

Administering an aerosolized drug in an air mixture containing up to about 10% carbon dioxide gas results in increased deposition of the drug in the respiratory system, measurably improving efficiency and therapeutic efficacy of the aerosol drug delivery. Preferred concentrations include 2.5%, 5% and 7.5% carbon dioxide gas. The aerosol may be administered for 1 to 30 minutes or even longer. The enhancing effect of the carbon dioxide is evident within 30 seconds. The respiratory effects of carbon dioxide are transient and can be employed repeatedly.

The following examples are given for the purpose of illustrating various embodiments of the invention and are not meant to limit the present invention in any fashion.

EXAMPLE 1

Materials

PTX was obtained from Xechem (New Brunswick, N.J.). CPT was obtained from Sigma (St. Louis, Mo.) and 9NC from ChemWerth (Woodbridge, Conn.). Dilauroylphosphatidylcholine (DLPC) was purchased from Avanti Polar Lipids (Alabaster, Ala.). DMSO was purchases from Sigma (St. Louis, Mo.) and HPLC grade other organic solvents were obtained from Fisher Scientific. Sterile water for irrigation came from Baxter Healthcare Corporation (Deerfield, Ill.).

ICR mice (7-8 weeks old) were obtained from Harlan-Sprague Dawley (Indianapolis, Ind.) and housed in standard cages with food and water provided ad libitum. Female C57BL/6 mice (8-9 weeks old) and female Balb/C mice (5-7 weeks old) were obtained from Harlan-Sprague Dawley (Houston, Tex.). All animal care was in accordance with Baylor College of Medicine Institutional Animal Care and Use Committee.

The bacterial chloramphenicol acetyl transferase gene (CAT, p4119, Ref. 15) is primarily used as the reporter gene for measuring transgene expression. The CAT gene is under the control of human cytomegalovirus (CMV) early promoter/enhancer element. The luciferase plasmid (pGL3, Promega, Madison, Wis.) modified by insertion of the CMV promoter/enhancer element and the human growth hormone polyadenylation sequence was a gift from Dr. Michael Barry (Center for Cell and Gene Therapy, Baylor). All plasmids are purified on Qiagen columns (Qiagen, Valencia, Calif.) and are endotoxin free. The plasmids are quantitated by UV absorbance at 260 nm. Agarose gel analysis is revealed th plasmids to be a mixture of primarily supercoiled plasmid with a small amount of nicked plasmid.

The plasmid containing the p53 gene was obtained from Dr. Y. K. Fung (Children's Hospital, Los Angeles, Calif.). The p53 gene is under the control of human cytomegalovirus (CMV) promoter/enhancer element. The plasmid used as a control contains the firefly luciferase (Luc) gene and was obtained from Dr. Michael Barry (Baylor College of medicine). The plasmids were purified commercially by Bayou Biolabs (Harahan, La.), were endotoxin free and were quantitated using UV absorbance. Agarose gel analysis revealed the plasmids to be primarily in the supercoiled form with a small amount of nicked plasmid.

B16-F10 melanoma cell line was obtained from Division of Cancer treatment and Diagnosis Center (DCTDC, NCE, Frederick, Md.) and cultivated in DMEM supplemented with 10% fetal calf serum. The cell line has been shown to form tumors in the lung (15). Twenty-five thousand B16-F10 cells in 200 μl of media are injected per mice via the tail vein of C57BL/6 mice. Lung metastases are visually detected within 2 weeks after inoculation of cells. The cells were used at passages 3-12.

EXAMPLE 2

Statistics

After performing one-way analysis of variance (ANOVA) to compare the means, a two-tailed unpaired Student's t test was done. A difference was considered significant if $P \leqq 0.05$.

EXAMPLE 3

Preparation of Liposomes

Stock solutions of DLPC, PTX and camptothecin are prepared in t-butanol at 100, 10 and 1 mg/ml, respectively, using previously described methods (17). Aliquots of paclitaxel and DLPC are mixed at a weight ratio of 1:10. The camptothecin to DLPC weight ratio is 1:50. The drug-phospholipid mixture is then frozen in liquid nitrogen and lyphilized overnight to a dry powder. The formulations are stored sealed at −20° C. Before use the mixture is reconstituted with sterile water for irrigation and vortexes until a homogeneous multi-lamellar liposomal suspension is obtained. The initial concentrations of camptothecin and paclitaxel in suspension prior to nebulization are 0.5 mg/ml and 10 mg/ml, respectively. The size of liposomes before and after nebulization is determined using Nicomp Submicron Particle Sizer Model 370 9NICOMP, Santa Barbara, Calif.).

EXAMPLE 4

Aerosol Particle Size Characteristics

The characteristics of aerosol particles containing liposomal encapsulated drugs are estimated using an Andersen/AFCM nonviable ambient particle sizing sampler (Andersen Instruments, Atlanta, Ga.) as described (31). The concentration of drug in aerosols produced by air or gas mixtures flowing at 10 L/min through AERO-MIST nebulizer is also measured by collecting samples for 3 min starting one minute after aerosolization initiation. The mass median aerodynamic diameter (MMAD) and geometric standard deviation (GSD) are calculated as described (30, 31) using KaleidaGraph 2.0 software (synergy Software, Reading, Pa.).

EXAMPLE 5

Aerosol Delivery of Paclitaxel and Camptothecin

The treatment of mice with aerosol is performed as previously described (16-18). Briefly, an AERO-MIST jet nebulizer (CIS-USA, Bedford, Mass.) is used to generate aerosol particles at the air flow rate of 10 L/min. Mice are placed in sealed plastic cage (23×18×13 cm) and exposed to aerosol for 30 min. The aerosol is generated with normal or 5% $CO_2$-enriched air obtained by mixing normal air and $CO_2$ with a blender (Bird 3m, Palm Springs, Calif.) and the $CO_2$ concentrations are calibrated with a Fluid Fyrite (Bacharach Inc., Pittsburgh, Pa.). At each time point 3 mice are removed from the cage and sacrificed by exposure to Isoflurane, USP (Abbott Laboratories, Chicago, Ill.) and exsanguination. Organs are resected, weighed and kept frozen at −70° C. until extraction.

EXAMPLE 6

Extraction of Drug From Tissues

Before extraction, samples are thawed and immediately cut in small pieces with scissors. To extract paclitaxel from tissues, 3 ml of ethylacetate is added to each sample and homogenized in a mini-beadbeater (Wig-L-Bud, Model 3110B, Crescent Dental MFR. Co., Lyons, Ill.) for 2 min. Homogenates are transferred to 10 ml conical glass centrifuge tubes and centrifuged at 1,000×g for 10 min. The supernatant fraction is separated and organic solvent is evaporated with air. The residue is reconstituted in 0.2 ml of methanol:acetonitrile (2:1, v/v), sonicated in a water-bath sonicator and centrifuged at 1,000×g for 10 min. Supernatant fractions are warmed at 37° C. for 30 min and analyzed by HPLC.

The extraction procedure for camptothecin and 9NC is as previously described (17). Briefly, after thawing tissue, 20 μg of 9NC in 20 μl is added in organs as an internal standard to determine the extraction efficiency. The samples are cut in small pieces and 1 ml of 0.1% aqueous acetic acid solution, pH 3.2 is added to each sample. After the homogenization in a mini-beadbeater, the homogenates are centrifuged at 1,000×g for 5 min. The supernatant fractions are re-extracted with 8 ml of methylene chloride. The organic fraction is separated and dried under air at room temperature. The dried samples are reconstituted in 0.2 ml of acetronitrile.

EXAMPLE 7

HPLC Analysis

Paclitaxel is quantified by reverse-phase HPLC monitoring on a Waters 486 UV absorbance detector at 227 nm (Waters, Milford, Mass.). All measurements are made at room temperature on Waters Nova-Pak C18 column (3.9×150 cm). The mobile phase is composed of 49% acetronitrile and 51% water. The flow rate ia 1.5 ml/min. A 25 μl aliquot of each sample is injected and data is analyzed with Waters millennium Software. For PIX extraction efficiency determination, identical procedures are performed when a known amount of paclitaxel is added to each tissue and compared to the extracted amount of paclitaxel. The extraction efficiency (%) is calculated as ((amount of paclitaxel after extraction)/(amount of added paclitaxel))×100. For all tested tissues the average extraction efficiency is 89±4% (data not shown) and this index is used to calculate the final concentrations of drug in the tissues.

HPLC analysis of camptothecin is performed using a Waters NovaPak C18 column (3.9×150 cm) (17). Chromatograms for camptothecin are monitored on Waters 470 scanning fluorescent detector (λex=360 nm, λem=455 nm) while 9NC is detected using Waters 440 UV absorbance detector monitoring at 254 nm. The mobile phase is composed of 30% acetonitrile and 70% of 0.1% acetic acid solution in water, pH 3.5 at a flow rate 1.2 ml/min (16,17).

EXAMPLE 8

Aerosol Characteristics of Liposome Formulations

The properties of CPT-DLPC and PTX-DLPC liposomes and their aerosol characteristics are summarized in Table 1. The utilization of 5%$CO_2$-air did not change the concentration of either drug in the aerosol or their MMAD and GSD ($P>0.1$; Student's t-test, two-tailed). The nebulization procedure reduces the size of liposome particles in solution from micron- to nano-particles for both drug formulations. The size of liposomes of CPT-DLPC decreased from 2.54±0.91 μm before nebulization to 0.49±0.07 μm after nebulization using the 5% $CO_2$-air mixture. For the PTX-DLPC formulation these values are 13.14±12.15 μm and 0.23±0.17 μm, respectively. The aerosol particle size before or after nebulization is not different for either PTX-DLPC or CPT-DLPC administered by aerosol using normal or 5% $CO_2$-air ($P>0.5$; Student's t-test, two-tailed).

TABLE 1

Aerosol and liposome characteristics for PTX-DLPC and CPT-DLPC formulations using 5% CO2-air versus normal air

| Drug Formulation | Air Composition | Drug Concentration in Aerosol, μg/L | Aerosol droplets MMAD μm | Aerosol droplets GSD | Liposome particle size, μm Before Nebulization | Liposome particle size, μm After Nebulization |
|---|---|---|---|---|---|---|
| CPT-DLPC, | Normal | 9.0 ± 1.3 | 1.6 ± 0.3 | 2.1 ± 0.1 | 3.72 ± 1.10 | 0.34 ± 0.11 |
| 0.5 mg CPT/ml | 5% CO2 | 9.2 ± 1.9 | 1.7 ± 0.5 | 2.3 ± 0.2 | 2.54 ± 0.91 | 0.49 ± 0.07 |
| PTX-DLPC, | Normal | 153.0 ± 27 | 2.0 ± 0.2 | 1.8 ± 0.03 | 12.49 ± 8.06 | 0.13 ± 0.18 |
| 10 mg PTX/ml | 5% CO2 | 175.0 ± 9 | 2.2 ± 0.2 | 1.9 ± 0.1 | 13.14 ± 12.15 | 0.23 ± 0.17 |

Values are means ± SD (n = 3 for each value).
MMAD, mass median aerodynamic diameter;
GSD, geometric standard deviation

EXAMPLE 9

Tissue Distribution and Pharmacokinetics of CPT-DLPC After Delivery by Aerosol Generated With Normal or 5% CO2-Enriched Air ICR mice are divided into two groups: the first group (n=4) received CPT-DLPC formulation via aerosol generated with normal air for 30 min, so their breathing parameters are not changed during treatment; the second group (n=6) inhaled the same formulation but in the atmosphere of 5% $CO_2$-enriched air.

Figure 1:
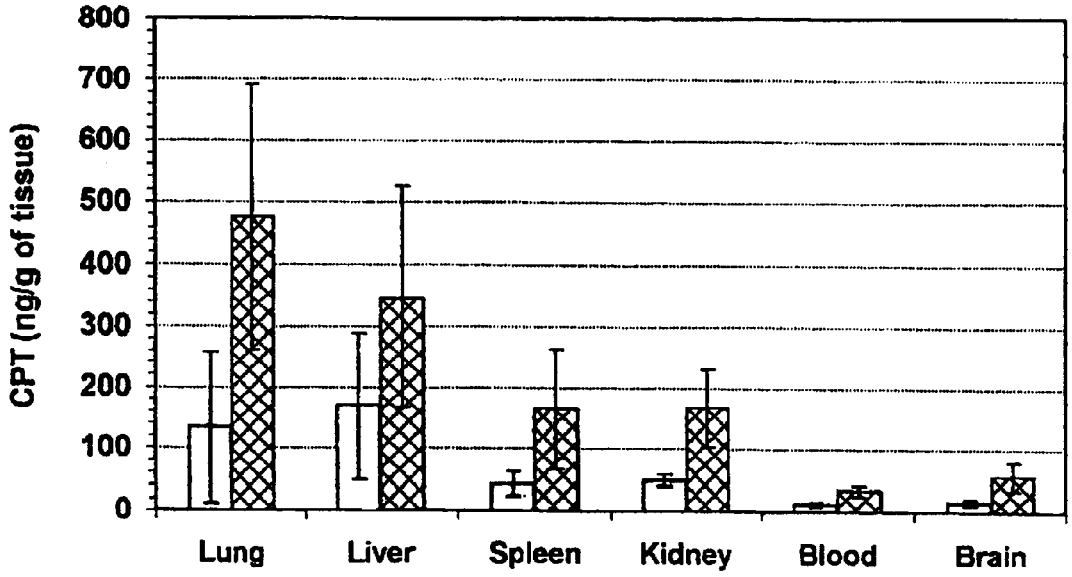
FIG. 1 shows the tissue distribution of camptothecin after a 30 min exposure to liposome aerosol generated with normal air (solid) or with 5% $CO_2$-enriched air (hatched). At the end of treatment (30 min) organs from three mice per group are resected and the drug content determined by HPLC. Mean values with SD are calculated. P values for 5% $CO_2$-air compared to normal air are 0.02, 0.13, 0.04, 0.04, 0.03, and 0/01 for lungs, liver, spleen, kidney, blood and brain, respectively (Student's t-test, two-tailed).

Inhalation of aerosols generated with 5% $CO_2$-air caused a significant increase in deposition of camptothecin into the lungs (2.1-3.5-fold) (FIG. 1). CPT is detected at 134±123 and 476±216 ng/g of lung tissue of mice from the first and second groups, respectively. The use of 5% $CO_2$-in-air did not change tissue distribution patterns. The concentrations of drug in the liver, spleen, kidney, blood and brain after inhalation of CPT-DLPC aerosol generated with 5% $CO_2$-air are also increased.

Figure 2:
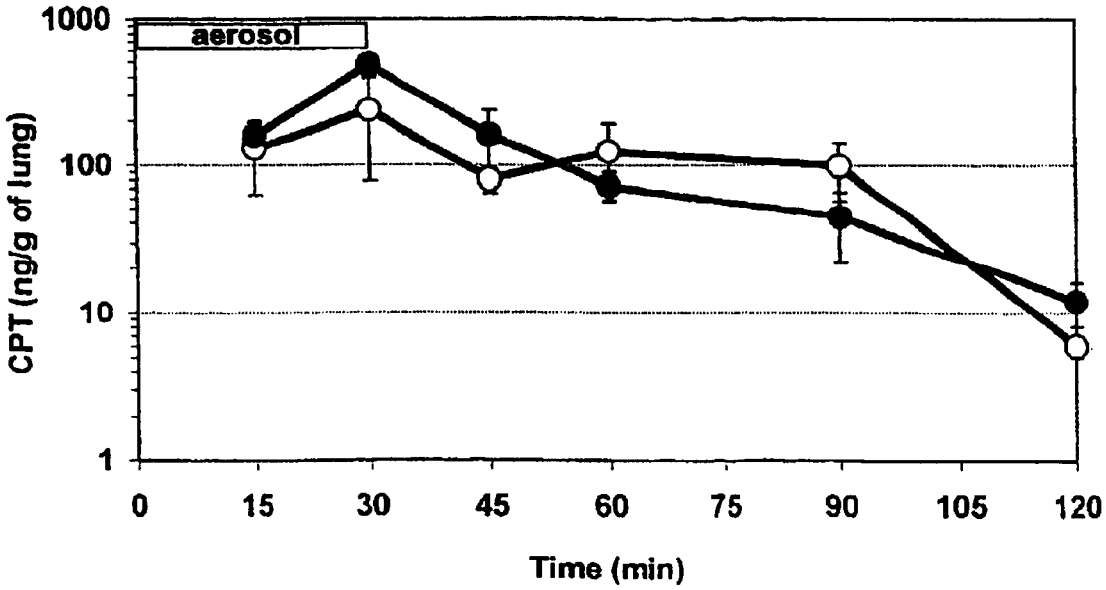
FIG. 2 shows the pulmonary concentration-time curve for CPT-liposomes administered for 30 min. by aerosol generated with normal air (O) or with 5% $CO_2$-enriched air (●). For each time point lungs from three mice are resected and the drug content determined by HPLC. Mean values with SD are calculated.

The pharmacokinetic deposition of camptothecin in lungs during and after 30 mins exposure to aerosols of CPT-DLPC using normal or 5% $CO_2$-air is determined (FIG. 2). The pulmonary concentrations of camptothecin increased during the treatment with the maximum concentration (Cmax) at the end of aerosol treatment (30 min.) and subsequently lung concentrations started to decline. The peak respiratory levels are 232±158 and 486±78 ng/g of the tissue for normal and 5% $CO_2$-air, respectively. During the 15 min after the aerosol has been stopped, the concentrations of the drug decrease exponentially. Clearing half-lives (T1/2) for both treatments are 12-15 min. The profiles of the pharmacokinetic curves are very similar for both types of treatment. Only trace amounts of drug are detected in the lungs 90 min. after the end of aerosolization (120 min. time point) with either air source.

EXAMPLE 10

Tissue Distribution and Pharmacokinetics of PTX Drug After Treatment With Aerosol PTX-DLPC Generated by Normal or 5% $CO_2$-Enriched Air Due to the limitations of the detection method, a liposomal formulation of paclitaxel at 10 mg of PTX/ml suspension is used. Mice are sacrificed halfway through exposure (15 min), at the end of treatment (30 min), and at several time points following the end of treatment. Mice are exposed to PTX-DLPC aerosol generated with either normal air or air containing 5% $CO_2$.

Figure 3:
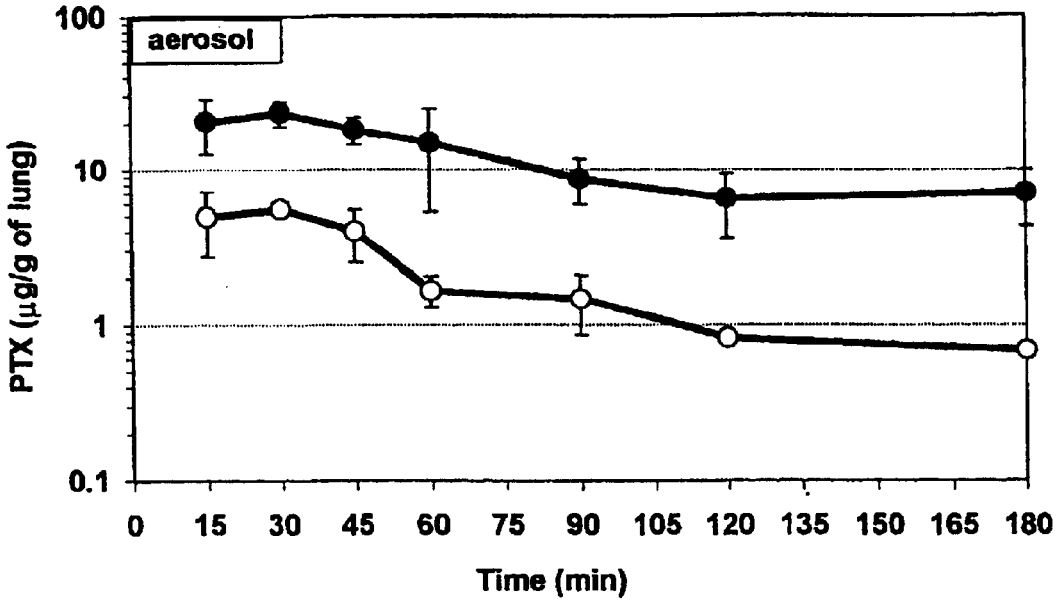
FIG. 3 shows the pulmonary concentration-time curve for PTX-liposomes administered for 30 min. by aerosol generated with normal air (O) or with 5% $CO_2$-enriched air (●).

Pulmonary paclitaxel Cmax values are achieved at the end of treatment (30 min) with either air source (FIG. 3). In the 5% $CO_2$-enriched air group Cmax is 4.2-fold higher than in the ambient air group (23.1±4.3 and 5.5±0.2 μg/g, respectively). This carbon dioxide induced enhancement is unrelated to the liposomal formulation (FIG. 4). Sterically stabilized paclitaxel liposomes prepared using dismyristylphosphoethanolamine poly (ethylene glycol) 2000 and dilauroylphosphatidylcholine are deposited in the lung at equivalent levels when 5% CO2-in-air is utilized.

Treatment with 5% CO2 produced 5.7-fold higher area under the lung-concentration-time curve compared to normal air (33.7 and 5.9 μg-hr/g, respectively). In both cases PTX concentrations started to decrease from the pulmonary tissue after the treatment ended. T1/2α and T1/2β values for paclitaxel in the lungs are 0.3 and 1.6 hr, respectively, when normal air is used for aerosol generation. T1/2α is 0.7 hr and T1/2β is 5.1 hr for paclitaxel administered by liposome aerosol produced with 5% $CO_2$-air. Comparative analysis for the other organs, such as liver, spleen, kidney and blood was performed; however, the levels of paclitaxel in these tissues using normal air for aerosolization are below detectable levels.

The tissue distribution of paclitaxel after liposome aerosol delivery using 5% $CO_2$-air is presented in Table 2. The highest concentration of the drug are detected in the lungs. Lower concentrations are found in the other organs. Analysis of the area under the concentration-time curve (AUC) over a 3 hr. period for different organisms using the trapezoidal rule shoes the following AUC values for lungs, liver, kidney, blood and brain: 34±2, 9.8±1.9, 2.4±1.4, 2.8±1.5, 0.13±0.10, 0.23±0.2 μg PTS-hr/g of tissue, respectively.

TABLE 2

| | PTX deposition in tissues during and after 30 min exposure to aerosol PTX-DLPC* generated with 5% CO2-air | | | | | |
|---|---|---|---|---|---|---|
| | PTX concentration (μg/g of tissue) | | | | | |
| Time (hr) | Lungs | Liver | Spleen | Kidney | Blood | Brain |
| 0.25 | 20.3 ± 7.8 | 1.5 ± 0.8 | 0.6 ± 0.3 | 1.4 ± 0.0 | 0.25 ± 0.03 | 0.14 ± 0.16 |
| 0.5 | 23.1 ± 4.3 | 5.7 ± 3.0 | 1.4 ± 0.9 | 1.6 ± 0.1 | 0.18 ± 0.08 | 0.16 ± 0.02 |
| 0.75 | 18.0 ± 3.6 | 5.5 ± 1.8 | 0.5 ± 0.4 | 1.4 ± 0.1 | 0.08 ± 0.09 | 0.11 ± 0.03 |
| 1.0 | 14.8 ± 9.5 | 4.8 ± 3.9 | 2.6 ± 2.7 | 1.2 ± 0.7 | 0.07 ± 0.07 | 0.11 ± 0.03 |
| 1.5 | 8.7 ± 2.8 | 2.8 ± 0.8 | 1.0 ± 1.6 | 0.7 ± 0.3 | 0.03 ± 0.06 | 0.09 ± 0.08 |
| 2.0 | 6.5 ± 2.9 | 3.1 ± 0.7 | 0.6 ± 0.4 | 0.4 ± 0.3 | 0.01 ± 0.02 | 0.04 ± 0.04 |
| 3.0 | 7.1 ± 2.8 | 9.3 ± 0.6 | 0.5 ± 0.2 | 0.4 ± 0.1 | 0.01 ± 0.02 | 0.05 ± 0.05 |

Values are means ± SD of three experiments (organs from 3 mice were combined and processed in each experiment

EXAMPLE 11

Effect of Carbon Dioxide Induced Respiratory Patterns on Drug Deposition

The increased pulmonary drug concentrations found in the lungs after inhalation of 5% $CO_2$-in-air could be explained by changed respiratory patterns. Breathing patterns of mice in the atmosphere of 5% $CO_2$-enriched air are visually observed to become deeper and slower and to return to normal almost immediately after the end of treatment. Histological analysis did not reveal any changes in pulmonary tissue. Plethysmograph studies that have been performed by other researchers have demonstrated that inhalation of 5% $CO_2$-enriched air increased ventilation in mammalians primarily because of the increase in tidal volume (approximately 170-180%) (18,19). The average pulmonary deposition of camptothecin and paclitaxel increased approximately 2-4-fold. This disproportion with the increased of tidal volume may be due to some other physiological changes in breathing parameters, e.g., breathing frequency, respiratory duration of inspiratory and expiratory cycles, and minute ventilation (13). By deep and complete expiration with breath holding the retention of the aerosol increased almost twice in comparison with normal breathing (15).

EXAMPLE 12

Preparation of PEI-DNA Complexes

PEI (25 kDa, branched) was purchased from Aldrich Chemical (Milwaukee, Wis.). A PEI stock solution was prepared at a concentration of 4.3 mg/ml (0.1 M in nitrogen) in PBS, pH 7-7.5. PEI and DNA are mixed separately in 5 ml water at the required concentrations. The PEI solution is slowly vortexed and the DNA solution is added to it to make a final volume of 10 ml. The mixture is alloed to stand at room temperature for about 15-20 min. before nebulization. The resulting charge ratio is expressed as PEI nitrogen:DNA phosphate (N:P), which can be calculated by taking into account that DNA has 3 nmol of phosphate per microgram and 1 μl of 0.1 M PEI solution has 100 nmol of amine nitrogen. A 10:1 N:P ratio corresponds to a 1:29:1 PEI:DNA weight ratio.

EXAMPLE 13

Aerosol Delivery of PEI:DNA Complexes

Mice are placed in plastic cages that are sealed with tape before aerosol delivery (48). This is an unrestrained, whole-body aerosol exposure system. PEI-DNA complexes are aerosolized using an Aero-Mist nebulizer (CIS-US, Inc., Bedford, Mass.) at 10 liters/min flow rate using air or air containing 5% CO2. Aero-Mist is a high-output, efficient nebulizer demonstrated to produce aerosols in the optimal range of 1-2 μm MMAD with a geometric standard deviation (GSD) of 2.9 using an Andersen cascade impactor (Andersen Instruments, Atlanta, Ga.) by a method previously described (50). A source of dry air (Aridyne 3500, Timeter, Lancaster, Pa.) is delivered to a Brid 3M gas blender (Palm Springs, Calif.) attached to an air compressor and a $CO_2$ tank. The resulting mixture of air and $CO_2$ is delivered to the nebulizer. The final concentration of 5% $CO_2$ in air is determined using a Fyrite solution (Bacharach, Pittsburgh, Pa.). Nebulization of 10 ml solution took approximately 30 min.

EXAMPLE 14

CAT Assay

Mice are anesthetized and sacrificed after each time point and the lungs and other tissues are harvested, weighted, and immediately frozen. A CAT ELISA kit (Boehringer Manheim GmbH, Mannheim, Germany) is used for measuring in vivo expression. The tissues are homogenized in 700 μl CAT assay lysis buffer using a Wig-L-Bug bead homogenizer (Crescent Dental Mfg., Lyons, Il). After centrifuging the homogenates, 200 μl of the extract is used for the CAT ELISA performed in a 96-well plate format. The absorbance is read using a microtiter plate reader (Molecular Devices, Sunnyvale, Calif.). Naive mice are used as controls. The CAT activity is expressed as ng of CAT/g of tissue using a standard curve prepared with purified CAT enzyme. The sensitivity of the assay is further enhanced according to suggestions from the manufacturer so that it can detect levels of CAT protein as low as 0.1-0.3 pg/well.

EXAMPLE 15

Luciferase Assay

Mice are anesthetized and sacrificed and the lungs are harvested. A luciferase assay kit (Promega) is used to measure luciferase expression. The lungs are homogenized in 1 ml of luciferase assay lysis buffer using a Wig-L-Bug bead homogenizer. After centrifuging the homogenates, 10 μl of the extract is added to 50 μl of luciferase substrates and the luminescence read for 10 s in a 96-well plate on a luminometer (Microlumat LB 96 P, EG & G Berthold, Germany). Naive mice are used as controls. The luciferase activity is expressed as RLU/10s/g of tissue. In this system, $10^7$ RLU corresponds to 1 ng of luciferase using purified luciferase from Promega.

EXAMPLE 16

Histological Analysis of Tissue Sections

Mice are anesthetized with isoflurane and sacrificed by exsanguination via the abdominal aorta. Lungs are isolated, cannulated, and fixed by inflation with 10% neutral buffered formalin, embedded in paraffin, and processed for histolgical analysis. Thin sections are cut at 4 μm and observed under the microscope for any sings of inflammation or toxicity using the hematoxylin and eosin stain.

EXAMPLE 17

Myeloperoxidase (MPO) Assay

Twenty-four hours after aerosol exposure, mice are anesthetized with isoflurane and sacrificed by exsanguination via the abdominal aorta. The lungs are harvested after perfusion through the heat with saline. The tissue is homogenized in hexadecyltrimethylammonium bromide (0.5% HTAB in 50 mM phosphate buffer, pH 6.0; 5 ml HTAB/g of tissue) as previously described (51). After centrifugation, the MPO activity in t h e supernatant is determined using o-diasinidine dihydrochloride (0.167 mg/ml) plus 0.0005% hydrogen peroxide. The absorbance is measured at 460 nm using a microtiter plate reader (Molecular Devices). The absolute values after 15 min are recorded. Naive mice are used as controls.

EXAMPLE 18

Nebulization of PEI-DNA Complexes With 5% $CO_2$ Enhances the Transgene Expression in Lung Compared to Normal Air Breathing 5% $CO_2$ in air has been associated with as increase in the tidal volume and breathing frequency in mice and humans (52-54). When 5% $CO_2$-in-air is utilized to deliver the PEI-DNA aerosol, the mice can be visually observed to be breathing deeper and more rapidly. Inhalation of aerosols containing 5% $Co_2$ could lead to greater inhalation of aerosol particles and correspondingly higher transgene expression compared to that achieved with aerosol delivered by air due to increased tidal volume and breathing frequency.

PEI-DNA complexes are delivered to Balb/C mice by aerosol using either normal air or air containing 5% $CO_2$. A fixed amount of CAT plasmid (1 mg/10 ml of solution), at a N:P ratio of 10:1, is aerosolized for 30 min as indicated above. The lungs are harvested after 24 h and CAT assay is performed to determine the degree of transfection. Five percent $CO_2$-in-air lead to a three-fold increase (P=0.001) in the levels of CAT detected compared to aerosol nebulized with air alone (FIG. 5). Also, 5% $CO_2$ does not change the particle size of the resulting drug-liposome aerosol particles.

Enhancement of PEI-DNA transfer to the lung b y aerosol using different percentages of $CO_2$-in-air with a fixed amount of CAT plasmid is also examined. The complexes are aerosolized using 0%, 2.5%, 5%, 10% and control amounts of carbon dioxide in air. The CAT activity assayed indicates using either 2.5% or 10% provides as good a level of transfection as using 5% $CO_2$-in air (FIG. 6).

It is possible that enhanced $CO_2$ has an effect on the transfection efficiency of PEI-DNA complexes by changing some other physiological parameters. However, $CO_2$ does not significantly alter the pH of the PEI-DNA solution nor does the particle size of the resulting aerosol droplets, as compared to those of air, significantly change. The increase in transgene expression in the lungs is most likely due to increased deposition of aerosol particles. Five percent $CO_2$-in-air also could help to optimize the aerosol delivery of other polymer-DNA or cationic lipid-DNA complexes (45). This percentage of $CO_2$ has been well tolerated by humans and has been shown to increase the minute volume (54,55), so this strategy could be efficacious against pulmonary diseases in humans provided that the size, geometry and physiology of the human pulmonary system is taken into consideration.

EXAMPLE 19

DNA Transfer by PET is Dose Dependent

To further optimize the transgene expression, the N:P ratio is kept constant at 10:1 and the amount of DNA is varied from 250 μg to 4 mg per 10 ml of the aerosolized solution. This leads to an increase in the reservoir concentration as well as the amount of total DNA nebulized in the aerosol output.

The nebulized output from the Aerotech II nebulizer was calculated to be approximately 80%. About 72% of the reservoir DNA was delivered to the inhalation chamber as estimated using an all-glass impinger (AGI) (50). The remainder was trapped in the T-connector and tubing. Based on murine obligate nasal breathing, pulmonary physiology (minute volume and deposition fraction) (50), and the output concentration of aerosol (4.8 ug/liter), the amount of DNA deposited in the lungs of a mouse is estimated to be approximately 4-5 μg during 30 min of aerosol exposure (for a starting reservoir concentration of 2 mg DNA/10 ml solution). These calculations are based on normal air breathing; the deposition could be higher in the presence of 5% $CO_2$ due to the increased tidal volume and breathing frequency (53).

The complexes are aerosolized using 5% $CO_2$-in-air with 2 mg DNA giving the highest level of CAT expression in the lung (FIG. 7). The levels of CAT measured with 250 μg DNA are not statistically different from control lungs (P=0.34). Also, when 4 mg of DNA is dissolved in 10 ml at a N:P ratio of 10:1, it leads to some visual precipitation of the DNA, whcih may account for no further increase in the level of CAT detected in the lungs compared to 2 mg (P=0.51).

It should be noted that there is an increase in both the concentration and the amount of DNA delivered. However, it may be possible to further increase the expression in the lung b y increasing the exposure time of aerosol at the optimal concentrations. These expression levels in the lung are comparable to those using other delivery systems (34).

EXAMPLE 20

Optimization of PEI-DNA Ratios

Although PEI can protect the DNA during nebulization and also result in higher transgene expression in the lungs after aerosol delivery when compared to most other cationic lipids, determination of optimal parameters for gene delivery is beneficial. The charge interaction between any cationic vehicle and the negatively charged DNA is an important factor determining the efficiency of the transfection of the complex. Previous studies have examined the optimum PEI-DNA (N:P) ratio for transfection in the lung (38, 56). However, these studies involved an intravenous mode of PEI-DNA delivery. Gene delivery by aerosol could require different conditions.

To determine the charge ratio that would be ideal for in vivo aerosol delivery, different PEI-DNA (N:P) ratios for their ability to transfect the lung are evaluated. The amount of DNA is kept constant at 2 mg and the PEI concentration is varied to obtain ratios of 5:1, 10:1, 12.5:1, 15:1, 17.5:1, and 20:1. These ratios are chosen based on previous in vitro and in vivo (by installation) studies (43). The complexes are aerosolized using 5% $CO_2$-in-air. A N:P ratio of 15:1 gave the highest level of CAT expression in lung, whereas 5:1 resulted in a very low level of CAT expression (FIG. 8). There is statistically no difference between 10:1, 12.5:1, 15:1, 17.5:1, and 20:1 ratios (P>0.1), but a significant difference between 15:1 and 20:1 (P=0.05) and between 10:1 and 15:1 (P=0.014).

To determine the optimal ratio for a plasmid other than CAT, different N:P ratios for the expression of the luciferase gene in the lung are tested. The ratios evaluated are 5:1, 10:1, 15:1, 20:1, 30:1, and 40:1. The optimum curve for luciferase shifted to the right compared to CAT, with the highest expression at 20:1 (P<0.05 compared to other ratios) (FIG. 8). This suggests that different plasmids might require different N:P ratios; the different size of luciferase plasmid leads to a structurally different complex with FE compared to that of the CAT plasmid. It could also be due to a difference in plasmid purity and the proportion of supercoiled structure. Still there is a considerable overlap in the optimum N:P ratios of these two plasmids. The optimum ratios for different plasmids may be different. Considering experimental variability, a ratio between 10:1 and 20:1 should work suitably. A ratio lower than 10:1 did not give very high transfection in the lung. These results are in agreement with those obtained using branched 25K PEI although the mode of delivery was intravenous (56).

EXAMPLE 21

Time Course of CAT Expression in Lung Following Single Aerosol Delivery

CAT expression was also used to monitor the time course of gene expression. The analysis of the persistence of CAT expression following a single aerosol delivery provides important information for planning a treatment regime for therapeutic studies. Two milligrams of CAT plasmid is aerosolized, using 5% $CO_2$-in-air, to the mice at two different N:P ratios, 15:1 and 10:1. Different time points examined for the 10:1 group are 1, 2, 3, and 6 days post aerosol exposure. Lungs and other tissues are harvested at different time points and frozen immediately. All tissues are assayed simultaneously after the last time point (day 6). For the 15:1 group the mice are sacrificed 1, 3, 7, and 10 days after aerosol treatments. The lungs are harvested, weighed, and frozen after each time point and the CAT protein is assayed after the last time point (day 10).

For both N:P ratios examined, the CAT expression is highest at 24 h and remains constant (statistically no difference between day 1 and day 3, P=0.4 for the 15:1 ratio and P=0.12 for the 10:1 ratio) for over three days (FIGS. 10A and 10B). The CAT level falls to about 50% of peak levels after a week and significant levels are detected even after 10 days (P=0.001 compared to control). This suggests that the delivery may be more than adequate for a variety of clinical applications. The persistence of gene expression up to day 10 is similar to or greater than that of other cationic lipids used for installation or aerosol delivery of genes (34,58).

EXAMPLE 22

Tissue distribution of Transgene

Intravenous or intraperitoneal delivery of DNA vectors generally results in expression in a variety of tissues. In order to determine if aerosol delivery of PEI-DNA results in systemic gene delivery, different tissues are harvested from the same group of mice as the above experiment (from the 10:1) group) and the CAT assay is performed after the last time point. The tissues examined are lung, liver, spleen, kidney, thymus, brain, and blood. The level of CAT detected in non-lung tissues was very low and not significantly different (P>0.1 for all the tissues) from the control tissues (FIG. 11).

The tissue distribution data show that gene expression following aerosol delivery in this system is confined to the lung, indicating minimal systemic delivery. In contrast to the lung, tissues such as liver, spleen, and kidney, which normally exhibit detectable levels of expression when genes are delivered via intravenous or intrapertioneal administration, exhibited insignificant or no detectable CAT expression when delivered by PEI-DNA aerosol. This is important if the expression of the gene of interest is to be restricted to the lungs. In other studies, the intratracheal mode of gene delivery has been used to localize the gene to the lungs (58). However, this is a rather invasive technique compared to aerosol and generally results in less uniform deposition to the peripheral regions of the lung. Aerosol delivery helps to distribute the particles noninvasively and uniformly through out the lungs (49).

EXAMPLE 23

Histological Analysis Shows No Signs of Inflammation

In order to determine if aerosol delivery of PEI-DNA complexes leads to any kind of toxicity or acute inflammation in this system, two milligrams of CAT plasmid is complexed with PEI at a N:P ratio of 15:1 and the mice are exposed to aerosol for 30 min using 5% $CO_2$-in-air. The mice are sacrificed after 24 h and the lungs are fixed in formalin and stained with hematoxylin and eosin. The lungs did not show any evidence of histological abnormality, e.g., inflammatory cell infiltration or damage to the lungs when thin sections are examined (FIG. 12). Use of 5% $CO_2$-in-air to optimize pulmonary gene delivery of PEI-DNA aerosol seems to be safe and highly specific for the lung.

Although high levels of expression are detected in this system even a week after single aerosol exposure, some therapies may require repeated and frequency delivery of genes. The effects of prolonged PEI-DNA aerosol exposure on lungs and other tissues needs to be determined.

EXAMPLE 24

Myeloperoxidase Assay Does Not Reveal Any Inflammation

Acute pulmonary inflammation is mediated in part by polymorphonuclear leukocyte (PMN) sequestration to the peripheral tissues. A biochemicl marker for polymorphonuclear leukocyte is myeloperoxidase (MPO), which is a heme-containing enzyme found in the azurophilic granules and its often utilized as an inflammation marker in the lungs (18). To assess neutrophil infiltration into the lungs, 2 mg of CAT plasmid is complexed with PEI at a N:P ratio of 15:1 and the mice are exposed to aerosol for 30 min using 5% $CO_2$-in-air. The mice are sacrificed after 24 h, the lungs were harvested, and the myeloperoxidase assay is performed (Table 3).

The myeloperoxidase contents in the control and aerosol-exposed lungs were not significantly different (P=0.92). The myeloperoxidase assay did not reveal any difference between the control and aerosol-exposed lungs, i.e., there is no difference in the absolute absorbance values (OD) between control and aerosol-exposed lungs, even 15 min after incubation of the reaction (OD of 0.078±0.009 for control and 0.084±0.004 for aerosol-exposed lungs, P>0.5).

TABLE 3

Myeloperoxidase (MPO) Assay for Evaluation of Neutrophil Infiltration into the Lungs

| Group | Control | Aerosol |
|---|---|---|
| Lung MPO activity (δA/min/g tissue) | 0.0398 ± 0.01 | 0.0404 ± 0.008 |

Note.
Two milligrams of CAT plasmid was complexed with PEI at a N:P ratio of 15:1 and the complex was aerosolized to five mice for 30 min using 5% CO2-in-air. Mice were sacrificed 24 h later, lungs were harvested, and the MPO assay was performed. Values are means ± SD (n = 5 mice per group).

EXAMPLE 25

P53 Assay

P53 expression was examined using an ELISA kit (Roche Diagnostics, Indianapolis, Ind.). For in vitro expression, B16-F10 cells grown in tissue culture plates (20,000 cells/well in a 48-well plate) were transfected with PEI:DNA complexes for 24 h. The cultures were then washed and cells lysed using cell lysis buffer. After centrifugation, 100 μl of the lysate was used for p53 ELISA. The p53 levels were normalized to the total protein content measured by the BCA protein assay (Pierce, Rockford, Ill.). For in vivo expression, mice were exposed to PEI:p53 aerosol, sacrificed 24 h later and the lungs harvested and weighed. The lungs were homogenized in 1 ml of ice cold cell lysis buffer (20 mM Tris, 0.5 mM EDTA, 1% Nonidet P40, 0.05% SDS, 1 mM PMSE, 1 μg/ml pepstatin, 2 μg/ml leupeptin) using a Wig-L-Bug bead homogenizer (Crescent, Lyons, Ill.). After centrifugation at 4° C., 100 μl of the supernatant was used for p53 ELISA performed in a 96-well plate. The absorbance (450 nm) was read in triplicate using a Molecular Devices (Sunnyvale, Calif.) microtiter plate reader. The amount of p53 was determined using a standard curve prepared with purified 053. The assay can detect p53 levels as low as 10 pg/ml and the linear measuring range of the assay is 50-1000 pg/ml. The total protein content in the lungs was determined using the BCA protein assay.

EXAMPLE 26

P53 Expression in Mouse Lung Following Aerosol Delivery of PEI-p53 Complexes PEI-p53 complexes are prepared as done for PEI:DNA complexes described above. Two milligrams of p53 plasmid is complexed with polyethylenimine at a PEI:DNA (N:P) ratio of 10:1 and aerosolized to the C57BL/6 mice using 5% $CO_2$-in-air. Mice were placed in plastic cages that were sealed with tape before aerosol delivery. This is an unrestrained, whole body aerosol exposure system. PEI-p53 complexes were aerosolized using an Aero-Mist nebulizer in the presence of 5% $CO_2$ as described for aerosolization of polyethyleneimine:CAT complexes previously herein.

P53 expression in lung was analyzed by ELISA 24 h after aerosol delivery of the PEI-p53 complexes to the mice. Aerosol delivery of complexes lead to about a four fold increase in the levels of p53 detected in the lung tissue compared to that detected in the lings of naive mice. The level of p53 in the control mice is 0.0398±0.01 pg/mg protein and the level in the aerosolized mice is 0.0404±0.008 pg/mg protein (values are means±SD) (59). Exposure to PEI-Luc did not result in any increase in the p53 levels (data not shown).

EXAMPLE 27

Inhibition of B16-F10 Lung Metastasis by Aerosol Delivery of PET-p53

C57BL/6 mice were injected intravenously with 25,000 B16-F10 cells on day 0. The mice were treated with polyethylenimine-p53 aerosol complexes generated using 5% $CO_2$ twice a week starting the day after inoculation of the cancer cells into the mice (on days 1, 4, 8, 11, 15, 18, and 22) with the last treatment on day 22 postinjection (a total of seven aerosol exposures). Control groups included untreated mice, mice treated with polyethyleneimine or with polyethylenimine-Luc aerosol complexes. The control animals start dying around day 24 post tumor cell inoculation, which is when the therapy was stopped and the experiment terminated. The dosage of treatment was 2 mg plasmid/10 ml of aerosolized solution at a polyethyleneimine:DNA (N:P) ratio of 10:1. This is the total amount of DNA aerosolized to the mice. The mount of DNA delivered per mouse is estimated to be about 4-5 μg in the presence of normal air and is increased in the presence of 5% $CO_2$ due to the increase in tidal and minute volumes.

On day 24 post tumor inoculation, the mice were sacrificed and the lungs fixed and tumor index was calculated. The mice treated with PEI-p53 has a very low tumor index (P<0.001 compared to all other groups) whereas all the control groups had large number of tumor nodules (FIGS. 13A, 13B). A majority of untreated mice and mice treated with either polyethylenimine alone or with polyethyleneimine-Luc had numerous uncountable tumor nodules with concomitant invasion into the chest wall and had metastases in extrapulmonary tissue such as the neck and abdominal lymph nodes. However, all of the mice treated with polyethyleneimine-p53 complexes had very small and distinct tumor foci with no invasion into the chest wall and no extrapulmonary metastatic tumors. There was no effect of 5% $CO_2$ alone on the growth of tumors compared to untreated mice (data not shown). The lung weights also showed a significant difference (P<0.0 1) between PEI-p53 treated group and all the control groups (FIG. 13C).

The following references are cited herein.

1. Persons et al., Airway deposition of hygroscopic heterodispersed aerosols: results of a computer model. J. Appl. Physiol. 63:1195-1204 (1987).
2. Persons et al., Maximization of pulmonary hygroscopic aerosol deposition. J. Appl. Physiol. 63: 1205-1209 (1987).
3. Schlenker, E. H. Ventilation and metabolism of the djungarian hamster (Phodopus sungorus) and the albino mouse. Comp. Biochem. Physiol. 82A:293-295 (1985).

4. Nielsen, et al., Ventilation, CO2 Production, and CO2 exposure effects in conscious, restrained CF-1 mice. Pharmacol. Toxicol. 72: 163-168 (1993).

5. Goldring, et al., Respiratory adjustment to chronic alkalosis in man. J. Clin. Inv. 47: 188-202.

6. Stegen, et al., Biological Psychology 49:109-122 (1998).

7. Hallman, M., et al., Inositol Supplementation in Premature Infants with Respiratory Distress Syndrome, N. Eng. J. Med. 326:1233-1239 (1992).

8. Knight, V., Viral and Mycoplasmal Infections of the Respiratory Tract. 1973, Lea and Febiger, Phila. Pa., pp. 2.

9. Kay, B., Allergy and Allergic Diseases, Blackwell Publications, Oxford, England, Vol. I pp. 730-741 (1997).

10. Burke, et al., Liposomal stabilization of camptothecin's lactone ring. J. Am. Chem. Soc. 114:8318 (1992).

11. Cabanes et al., Comparative in vivo studies with paclitaxel and liposome-encapsulated paclitaxel. Int. J. Oncol. 12: 1035 (1998).

12. Daoud, et al., Antitumor effect of liposome-incorporated camptothecin in human malignant xenografts. Anticancer Drugs 6: 83 (1995).

13. Davis, J. N. and Staag, D. Interrelationships of the volume and time components of individual breaths in resting man. J. Physiol. 245: 481 (1975).

14. Gottschalk, et al., Fundamental investigations for the deposition of aerosols from radioactive solutions in the upper and lower airways. Z. Erkr Atmungsorgane 153: 355 (1979).

15. Hershey, et al., Inhalation chemotherapy for macroscopic primary or metastatic lung tumors: proof of principle using dogs with spontaneously occurring tumors as a model. Clin. Cancer Res. 5: 2653 (1999).

16. Knight et al., Anticancer effect of 9-nitrocamptothecin liposome aerosol on human cancer xenografts in nude mice. Cancer Chemother. Pharmacol. 44: 177 (1999).

17. Koshkina, et al., Distribution of camptothecin after delivery as a liposome aerosol or following intramuscular injection in mice. Cancer Chemother. Pharmacol. 44: 187 (1999).

18. Koshkina, et al., 9-Nitrocamptothecin liposome aerosol treatment of melanoma and osteosarcoma lung metastases in mice. Clin. Cancer Res. (in press).

19. Mortola, J.P. and Lanthier, C. Theventilatory and metabolic response to hyprcapnia in newborn mammalian species. Respiration Physiol. 103:263.

20. Nielsen, et al., Ventilation, CO2 production, and CO2 exposure effects in conscious, restrained CF-1 mice. Phrmcol Toxicol. 72:163 (1993).

21. Rajkumar, S. V. and Adjei, A. A. A review of the pharmacology and clinical activity of new chemotherapeutic agents in lung cancer. Cancer Treat Rev. 24: 35-3 (1998).

22. Rowinsky, E. K. and donehower, R. C. Drug therapy: paclitaxel (Taxol). N. Engl. J. Med. 332: 1004 (1995).

23. Sharma, et al., Activity of paclitaxel liposome formulations against human ovarian tumor xenografts. Int. J. Cancer 71: 103 (1997).

24. Socinski, M. A. Single-agent paclitaxel in treatment of advanced non-small lung cancer. Oncologist 4: 408 (1999).

25. Stehlin, et al., Phase I clinical trail and pharmacokinetics results with oral administration of 20-(S)-camptothecin. In: Potmesil M., Pinedo, H., eds. Camptothecins, new anticancer agents. CRC Press. Boca Raton, Fla.: 59 (1995).

26. Steward, W. P. and Dunlop, D. J. New drugs in the treatment of non-small cell cancer. Ann. Oncol. 6: S49 (1995).

27. Sugarman, et al., Lipid-complexed camptothecin: formulation andinitial biodistribution and antitumor activity studies. Cancer Chemother. Parmacol. 37: 531 (1996).

28. Verschraegen, et al., A phase I clinical and pharmacological study of oral 9-nitrocamptothecin, a novel water-insoluble topoisomerase I inhibitor. Anti-Cancer Drugs 9: 36 (1998).

29. Vidgren, et al., A study of $^{99m}$technetium-labelled beclomethasone dipropionate dilauroylphosphatidylcholine liposome aerosol in normal volunteers. Int. J. Pharm. 115: 209 (1999).

30. Waldrep, et al., Operating characteristics of 18 different continuous-flow jet nebulizers with beclomethasone dipropionate liposome aerosol. Chest 105: 106 (1994).

31. Waldrep, et al., High does cyclosporin A and budesonide-liposome aerosols. Int. J. Pharm. 12: 27 (1997).

32. Yamashiro, et al., Total work rate of breathing optimization in CO2-inhalation and exercise. J. Appl. Physiol. 38: 702 (1975).

33. Templeton et al., Improved DNA:lipsomoe complexes for increased systemic delivery and gene expression. Nat. Biotechnol. 15: 647-652 (1997).

34. Eastman, S. J., et al. A concentrated and stable aerosol formulation of cationic lipid:DNA complexes giving high level gene expression in mouse lung. Hum. Gene Ther. 8: 165-773 (1997).

35. Li, S., and Huang, L. In vivo gene transfer via intravenous administration of cationic lipid-orotamine-DNA (LPD) complexes. Gen. Ther:. 4:891-900 (1997).

36. Boussif, O., et al. A versatile vector for gene and oligonucleotide transfer into cells in culture and in vivi: Polyethyleneimine. Proc. Natl. Acad. Sci, USA 92:7297-7301 (1995).

37. Godbey, et al., Tracking the intercellular path of poly (ethylenimine)/DNA complexes for gene therapy. Proc. Natl. Acad. Sci. USA 90: 5177-5181 (1999).

38. Ferrari, et al., Polyethylenimine shows properties of interest for cystic fibrosis gene therapy. Biochim. Biophys. Acta 1447: 219-225 (1999).

39. Goula, et al., Polyethylenimine-based intravenous delivery of transgenes to mouse lung. Gene Ther. 5: 1291-1295 (1998).

40. Abdallah, et al., A powerful nonviral vector for in vivo gene transfer into the adult mammalian brain: Polyethylenimine. Hum. Gene. Ther. 7: 1947-1954 (1996).

41. Boleta, et al., Nonviral gene delivery to rat kidney with polyethyleneimine. Hum. Gene. Ther. 8: 1243-1251 (1997).

42. Coll, et al., In vivo delivery to tumors fDNA complexed with linear polyethylenimine. Hum. Gene Ther. 10: 1659-1666 (1999).

43. Schwartz, et al., Delivery of DNA-cationic liposome complexes by small particle aerosol. Hum. Gene Ther. 7: 731-741 (1996).

44. Densmore, C. L., et al. Aerosol delivery of robust polyethyleneimine-DNA complexes for gene therapy and genetic immunization. Mol. Ther. 1: 180-188 (2000).

45. Densmore, et al., Gene transfer by guanidiumcholesterol:dioleoylphosphatidylethanolamine liposome-DNA complexes in aerosol. J. Gene Med. 1: 251-264 (1999).

46. Ernst, N., et al. Interactions of liposomal and polycationic transfection complexes with pulmonary surfactant. J. Gene Med. 1: 331-340 (1999).

47. Liu, et al., Cationic liposome-mediated intravenous gene delivery. J. Biol. Chem. 270: 24864-24870 (1995).

48. Koshkina, et al., Distribution of camptothecin after delivery as a liposome aerosol or following intramuscular infection in mice. Cancer Chemother. Pharmocol. 44: 187-192 (1999).

49. Vidgren, M. et al. A study of 99mtchnetium-labeled beclomethasone dipropionate dilauroylphosphatidylcholine liposome aerosol in normal volunteers. Int. J. Pharm. 115: 209-216(1995).

50. Knight, et al., Anticancer effect of 9-nitrocamptothecin liposome aerosol on human cancer xenografts in nude mice. Cancer Chemother. Pharmacol. 44:177-186 (1999).

51. Goldblum, et al., Lung myeloperoxidase as a measure of pulmonary leukostasis in rabbits. J. Appl/ Physiol. 59: 1978-1985 (1985).

52. Schlenker, E. H. Ventilation and metabolism of the djungarian hamster (phodopus sungorus) and the albino mouse. Comp. Biochem. Physiol 82A: 293-295 (1985).

53. Nielsen, et al., Ventilation, CO2 production and CO2 exposure effects in conscious, restrained CF-1 mice. Pharmacol. Toxicol. 72: 163-168 (1993).

54. Goldring, et al., Respiratory adjustment to chronic metabolic alkalosis in man. J. Clin. Invest. 47: 188-202 (1968).

55. Goldring, et al., Regulation of alveolar ventilation in respiratory failure. Am. J. Med. Sci. 269: 160-170 (1975).

56. Bagonzi, A., et al. Comparison between cationic polymers and lipids in mediating systemic gene delivery to the lungs. Gene Ther. 6: 1995-2004 (1999).

57. Lee, E. R., et al. Detailed analysis of structure and formulations of cationic lipids for efficient gene transfer to lung. Hum. Gene ther. 7: 1701-1717 (1996).

58. Meyer, et al., Intratracheal gene delivery to mouse airway: Characterization of plasmid DNA expression and pharmacokinetics. Gene Ther. 2: 450-460 (1995).

59. Fidler, I. J., and Nicolson, G. L. Tumor cell and host properties affecting the implantation and survival of blood-borne metastatic variants of B16 melanoma Isr. J. Med. Sci. 14:38-50 (1978).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of increasing the deposition of a drug into the respiratory tract of an individual or animal during inhalation therapy, comprising the steps of:

mixing carbon dioxide gas with air to form a carbon dioxide-air mixture, said carbon dioxide-air mixture containing bout 7.5% to about 10% by volume carbon dioxide gas;

aerosolizing said drug in said carbon dioxide-air mixture wherein prior to aerosolization said drug is a soluble drug dissolved in a buffered solution or water or, in the alternative, said drug is an insoluble or lipophilic drug carried by a liposome, a sterically stabilized liposome, a slow release polymer or a polycationic polymer; and administering said aerosolized drug during inhalation therapy by continuously flowing said carbon-dioxide-air mixture wherein carbon dioxide in said mixture increases inhalation rate and inhaled volume of said aerosolized drug thereby increasing deposition of said aerosolized drug into the respiratory tract.

2. The method of claim 1, wherein said aerosol is administered for a period of time from about 1 minute to about 30 minutes.

3. The method of claim 1, wherein said drug is aerosolized by a jet nebulizer.

4. The method of claim 1, wherein said water soluble or buffer soluble drug is selected from the group consisting of an antibiotic, a mucolytic, a bronchodilator, a parasympathetic agent, an enzyme and an anti-viral.

5. The method of claim 1, wherein said sterically stabilized liposome is a poly(ethylene glycol) modified phospholipid.

6. The method of claim 5, wherein said poly(ethylene glycol) modified phospholipid is dimyristoylphosphoethanolamine poly(ethylene glycol) 2000.

7. The method of claim 1, wherein said lipophilic drug is selected from the group consisting of amphotericin B, nystatin, glucocorticoids, an immunosuppressive and an anti-cancer drug.

8. The method of claim 7, wherein said anti-cancer drug is selected from the group consisting of camptothecin, 9-nitrocamptotecin, and paclitaxel.

9. The method of claim 1, wherein said drug is selected from the group consisting of therapeutic proteins, therapeutic peptides, DNA genes, sense oligonucleotides, anti-sense oligonucleotides and viral vectors.

10. The method of claim 9, wherein said DNA gene is chloramphenicol acetyl transferase or p53.

11. The method of claim 9, wherein said DNA gene is delivered via a polycationic polymer carrier.

12. The method of claim 11, wherein said polycationic polymer is polyethylenimine.

13. The method of claim 12, wherein a ratio of polyethylenimine nitrogen to DNA phosphate (nitrogen:phosphate) is about 10:1 to about 20:1.

14. The method of claim 13, wherein said polyethylenimine nitrogen:DNA phosphate ratio is 10:1.

15. The method of claim 1, wherein said liposome is formed from a lipid comprising a phosphatidylcholine.

16. The method of claim 15, wherein said phosphatidylcholine is dilauroylphosphatidylcholine.

*17. A method of increasing the deposition of a drug into the respiratory tract of a human, comprising the steps of:*

*mixing carbon dioxide gas with air to form a carbon dioxide-air mixture, said carbon dioxide-air mixture containing up to 10% by volume carbon dioxide gas;*

*aerosolizing said drug in said carbon dioxide-air mixture; and*

*administering said aerosolized drug to a human during inhalation therapy, wherein carbon dioxide in said mixture increases inhalation rate and inhaled volume of said aerosolized drug thereby increasing deposition of said aerosolized drug into the respiratory tract.*

*18. The method of claim 17, wherein said aerosol is administered for a period of time from about 1 minute to about 30 minutes.*

*19. The method of claim 17, wherein said drug is aerosolized by a jet nebulizer.*

*20. The method of claim 17, wherein said carbon dioxide-air mixture contains about 2.5% by volume carbon dioxide gas.*

*21. The method of claim 17, wherein said carbon dioxide-air mixture contains about 5% by volume carbon dioxide gas.*

*22. The method of claim 17, wherein said carbon dioxide-air mixture contains about 7.5% by volume carbon dioxide gas.*

*23. A method of increasing the deposition of a drug into the respiratory tract of an individual or animal during inhalation therapy, comprising the steps of:*

*mixing carbon dioxide gas with air to form a carbon dioxide-air mixture, said carbon dioxide-air mixture containing up to about 10% by volume carbon dioxide gas;*

*aerosolizing said drug in said carbon dioxide-air mixture wherein prior to aerosolization said drug is a soluble drug dissolved in a buffered solution or water; and*

*administering said aerosolized drug during inhalation therapy by continuously flowing said carbon-dioxide-air mixture wherein carbon dioxide in said mixture increases inhalation rate and inhaled volume of said aerosolized drug thereby increasing deposition of said aerosolized drug into the respiratory tract.*

*24. The method of claim 21, wherein said aerosol is administered for a period of time from about 1 minute to about 30 minutes.*

*25. The method of claim 23, wherein said drug is aerosolized by a jet nebulizer.*

*26. The method of claim 23, wherein said water soluble or buffer soluble drug is selected from the group consisting of an antibiotic, a mucolytic, a bronchodilator, a parasympathetic agent, an enzyme and an anti-viral agent.*

*27. The method of claim 23, wherein said carbon dioxide-air mixture contains about 2.5% by volume carbon dioxide gas.*

*28. The method of claim 23, wherein said carbon dioxide-air mixture contains about 5% by volume carbon dioxide gas.*

*29. The method of claim 23, wherein said carbon dioxide-air mixture contains about 7.5% by volume carbon dioxide gas.*

*30. A method of increasing the deposition of a drug into the respiratory tract of an individual or animal during inhalation therapy, comprising the steps of:*

*mixing carbon dioxide gas with air to form a carbon dioxide-air mixture, said carbon dioxide-air mixture containing up to about 10% by volume carbon dioxide gas;*

*aerosolizing said drug in said carbon dioxide-air mixture wherein prior to aerosolization said drug is a lipophilic drug carried by a liposome, wherein said lipophilic drug is selected from the group consisting of amphotericin B, nystatin, glucocorticoids, an immunosuppressive, and an anti-cancer drug; and*

*administering said aerosolized drug during inhalation therapy by continuously flowing said carbon-dioxide-air mixture wherein carbon dioxide in said mixture increases inhalation rate and inhaled volume of said aerosolized drug thereby increasing deposition of said aerosolized drug into the respiratory tract.*

*31. The method of claim 30, wherein said aerosol is administered for a period of time from about 1 minute to about 30 minutes.*

*32. The method of claim 30, wherein said drug is aerosolized by a jet nebulizer.*

*33. The method of claim 30, wherein said anti-cancer drug is selected from the group consisting of captothecin, 9-nitrocamptothecin, and paclitaxel.*

*34. The method of claim 30, wherein said liposome is a sterically stabilized liposome.*

*35. The method of claim 34, wherein said sterically stabilized liposome is a poly(ethylene glycol) modified phospholipid.*

*36. The method of claim 35, wherein said poly(ethylene glycol) modified phospholipid is dimyristoylphosphoethanolamine poly(ethylene glycol) 2000.*

*37. The method of claim 30, wherein said liposome is formed from a lipid comprising a phosphatidylcholine.*

*38. The method of claim 37, wherein said phosphatidylcholine is dilauroylphosphatidylcholine.*

*39. The method of claim 30, wherein said carbon dioxide-air mixture contains about 2.5% by volume carbon dioxide gas.*

*40., The method of claim 30, wherein said carbon dioxide-air mixture contains about 5% by volume carbon dioxide gas.*

*41. The method of claim 30, wherein said carbon dioxide-air mixture contains about 7.5% by volume carbon dioxide gas.*

*42. A method of increasing the deposition of a drug into the respiratory tract of an individual or animal during inhalation therapy, comprising the steps of:*

*mixing carbon dioxide gas with air to form a carbon dioxide-air mixture, said carbon dioxide-air mixture containing up to about 10% by volume carbon dioxide gas;*

*aerosolizing said drug in said carbon dioxide-air mixture wherein said drug is carried by a polymer or a slow release polymer or polycationic polymer; and*

*administering said aerosolized drug during inhalation therapy by continuously flowing said carbon-dioxide-air mixture wherein carbon dioxide in said mixture increases inhalation rate and inhaled volume of said aerosolized drug thereby increasing deposition of said aerosolized drug into the respiratory tract.*

*43. The method of claim 42, wherein said aerosol is administered for a period of time from about 1 minute to about 30 minutes.*

*44. The method of claim 42, wherein said drug is aerosolized by a jet nebulizer.*

*45. The method of claim 42, wherein said drug is selected from the group consisting of therapeutic proteins, therapeutic peptides, DNA genes, sense oligonucleotides, anti-sense oligonucleotides, and viral vectors.*

*46. The method of claim 45, wherein said DNA gene is chloramphenicol acetyl transferase or p53.*

*47. The method of claim 42, wherein said polycationic polymer is polyethylenimine.*

*48. The method of claim 47, wherein as ratio of polyethylenimine nitrogen to DNA phosphate (nitrogen:phosphate) is about 10:1 to about 20:1.*

*49. The method of claim 48, wherein said polyethylenimine nitrogen:DNA phosphate ratio is 10:1.*

*50. The method of claim 42, wherein said carbon dioxide-air mixture contains about 2.5% by volume carbon dioxide gas.*

*51. The method of claim 42, wherein said carbon dioxide-air mixture contains about 5% by volume carbon dioxide gas.*

*52. The method of claim 42, wherein said carbon dioxide-air mixture contains about 7.5% by volume carbon dioxide gas.*

* * * * *

UNITED STATES PATENT AND TRADEMARK OFFICE

CERTIFICATE OF CORRECTION

PATENT NO. : RE 40,300 E
APPLICATION NO. : 10/927663
DATED : May 6, 2008
INVENTOR(S) : J. Clifford Waldrep et al.

It is certified that error appears in the above-identified patent and that said Letters Patent is hereby corrected as shown below:

In claim 1, column 24, line 14, delete “bout” and insert --about-- therefor.

In claim 4, column 24, line 35, after “anti-viral”, insert --agent--.

In claim 8, column 24, line 48, delete “nitrocamptotecin” and insert --nitrocamptothecin-- therefor.

In claim 24, column 25, line 43, delete “21” and insert --23-- therefor.

In claim 33, column 26, line 18, delete “captothecin” and insert --camptothecin-- therefor.

In claim 40, column 26, line 34, after “40.”, delete the comma.

In claim 48, column 27, line 1, delete “as” and insert --a-- therefor.

Signed and Sealed this

Twenty-ninth Day of July, 2008

JON W. DUDAS
*Director of the United States Patent and Trademark Office*